(12) United States Patent
Edwards et al.

(10) Patent No.: US 6,974,456 B2
(45) Date of Patent: Dec. 13, 2005

(54) METHOD TO TREAT GASTRIC REFLUX VIA THE DETECTION AND ABLATION OF GASTRO-ESOPHAGEAL NERVES AND RECEPTORS

(75) Inventors: Stuart D. Edwards, Portola Valley, CA (US); John W. Gaiser, Mountain View, CA (US); David S Utley, San Carlos, CA (US)

(73) Assignee: Curon Medical, Inc., Fremont, CA (US)

( * ) Notice: Subject to any disclaimer, the term of this patent is extended or adjusted under 35 U.S.C. 154(b) by 1 day.

(21) Appl. No.: 10/156,505

(22) Filed: May 28, 2002

(65) Prior Publication Data

US 2002/0138075 A1 Sep. 26, 2002

Related U.S. Application Data

(63) Continuation of application No. 09/410,448, filed on Oct. 1, 1999, now Pat. No. 6,405,732, which is a continuation-in-part of application No. 09/026,086, filed on Feb. 19, 1998, now Pat. No. 6,006,755.

(51) Int. Cl.[7] .............................................. A61B 18/18
(52) U.S. Cl. ........................................ 606/41; 607/133
(58) Field of Search ............................. 606/41, 42, 45, 606/46–50; 607/101, 102, 116, 122, 133; 128/898

(56) References Cited

U.S. PATENT DOCUMENTS

| | | |
|---|---|---|
| 1,798,902 A | 3/1931 | Raney |
| 3,517,128 A | 6/1970 | Hines |
| 3,901,241 A | 8/1975 | Allen, Jr. |

(Continued)

FOREIGN PATENT DOCUMENTS

| | | |
|---|---|---|
| DE | 43 03 882 | 2/1995 |
| DE | 38 38 840 | 2/1997 |
| EP | 0 139 607 | 5/1985 |

(Continued)

OTHER PUBLICATIONS

Castell, D.O. "Gastroesophageal Reflux Disease: Current Strategies for Patient Management." Arch Fam Med. 5(4): 221–7.

(Continued)

*Primary Examiner*—Michael Peffley
(74) *Attorney, Agent, or Firm*—Ryan Kromholz & Manion, S.C.

(57) ABSTRACT

The present invention comprises a method of treating a sphincter that provides a sphincter electropotential mapping device with at least one of a mapping electrode or a treatment electrode. The sphincter electropotential mapping device is introduced into at least a portion of the sphincter, the lower esophageal sphincter, stomach, the cardia or the fundus. Bioelectric activity causing a relaxation of the sphincter is detected and energy is delivered from either the mapping electrode or the treatment electrode to treat the bioelectric activity.

In another embodiment of the method of the invention, a method of treating a sphincter that provides a sphincter electropotential mapping device with at least one of a mapping electrode or a treatment electrode. The sphincter electropotential mapping device is introduced into at least a portion of the sphincter, the lower esophageal sphincter, stomach, the cardia or the fundus. The sphincter, lower esophageal sphincter, stomach, cardia or fundus is stimulated to produce a transient relaxation of the sphincter. The portion of the sphincter, lower esophageal sphincter, stomach, cardia or fundus causing a relaxation of the sphincter is indentified. Energy is delivered from the sphincter electropotential mapping device to treat the portion the sphincter, lower esophageal sphincter, stomach, cardia or fundus causing the transient relaxation of the sphincter.

7 Claims, 34 Drawing Sheets

U.S. PATENT DOCUMENTS

| | | |
|---|---|---|
| 4,011,872 A | 3/1977 | Komiya |
| 4,196,724 A | 4/1980 | Wirt et al. |
| 4,411,266 A | 10/1983 | Cosman |
| 4,423,812 A | 1/1984 | Sato |
| 4,532,924 A | 8/1985 | Auth et al. |
| 4,565,200 A | 1/1986 | Cosman |
| 4,705,041 A | 11/1987 | Kim |
| 4,901,737 A | 2/1990 | Toone |
| 4,906,203 A | 3/1990 | Margrave et al. |
| 4,907,589 A | 3/1990 | Cosman |
| 4,943,290 A | 7/1990 | Rexroth et al. |
| 4,947,842 A | 8/1990 | Marchosky et al. |
| 4,955,377 A | 9/1990 | Lennox et al. |
| 4,966,597 A | 10/1990 | Cosman |
| 4,976,711 A | 12/1990 | Parins et al. |
| 5,019,075 A | 5/1991 | Spears et al. |
| 5,035,696 A | 7/1991 | Rydell |
| 5,046,512 A | 9/1991 | Murchie |
| 5,047,028 A | 9/1991 | Qian |
| 5,057,107 A | 10/1991 | Parins et al. |
| 5,078,717 A | 1/1992 | Parins et al. |
| 5,083,565 A | 1/1992 | Parins |
| 5,084,044 A | 1/1992 | Quint |
| 5,088,979 A | 2/1992 | Filipi et al. |
| 5,094,233 A | 3/1992 | Brennan |
| 5,100,423 A | 3/1992 | Fearnot |
| 5,106,360 A | 4/1992 | Ishiwara et al. |
| 5,122,137 A | 6/1992 | Lennox |
| 5,125,928 A | 6/1992 | Parins et al. |
| 5,156,151 A * | 10/1992 | Imran .......................... 600/375 |
| 5,190,541 A | 3/1993 | Abele et al. |
| 5,197,963 A | 3/1993 | Parins |
| 5,197,964 A | 3/1993 | Parins |
| 5,205,287 A | 4/1993 | Erbel et al. |
| 5,215,103 A | 6/1993 | Desai |
| 5,228,442 A * | 7/1993 | Imran .......................... 600/374 |
| 5,232,444 A | 8/1993 | Just et al. |
| 5,236,413 A | 8/1993 | Fiering |
| 5,242,441 A | 9/1993 | Avitall |
| 5,254,126 A | 10/1993 | Filipi et al. |
| 5,256,138 A | 10/1993 | Vurek et al. |
| 5,257,451 A | 11/1993 | Edwards et al. |
| 5,263,493 A | 11/1993 | Avitall |
| 5,275,162 A | 1/1994 | Edwards et al. |
| 5,275,608 A | 1/1994 | Forman et al. |
| 5,275,610 A | 1/1994 | Eberbach |
| 5,277,201 A | 1/1994 | Stern |
| 5,281,216 A | 1/1994 | Klicek |
| 5,281,217 A | 1/1994 | Edwards et al. |
| 5,281,218 A | 1/1994 | Imran |
| 5,290,286 A | 3/1994 | Parins |
| 5,292,321 A | 3/1994 | Lee |
| 5,293,869 A | 3/1994 | Edwards et al. |
| 5,309,910 A | 5/1994 | Edwards et al. |
| 5,313,943 A | 5/1994 | Houser et al. |
| 5,314,466 A | 5/1994 | Stern et al. |
| 5,316,020 A | 5/1994 | Truffer |
| 5,324,284 A * | 6/1994 | Imran .......................... 606/15 |
| 5,328,467 A | 7/1994 | Edwards et al. |
| 5,334,196 A | 8/1994 | Scott et al. |
| 5,336,222 A | 8/1994 | Durgin, Jr. et al. |
| 5,345,936 A | 9/1994 | Pomeranz et al. |
| 5,348,554 A | 9/1994 | Imran et al. |
| 5,363,861 A | 11/1994 | Edwards et al. |
| 5,365,926 A | 11/1994 | Desai |
| 5,365,945 A | 11/1994 | Halstrom |
| 5,366,490 A | 11/1994 | Edwards et al. |
| 5,368,557 A | 11/1994 | Nita et al. |
| 5,368,592 A | 11/1994 | Stern et al. |
| 5,370,675 A | 12/1994 | Edwards et al. |
| 5,370,678 A | 12/1994 | Edwards et al. |
| 5,383,876 A | 1/1995 | Nardella |
| 5,383,917 A | 1/1995 | Desai et al. |
| 5,385,544 A | 1/1995 | Edwards et al. |
| 5,397,339 A | 3/1995 | Desai |
| 5,398,683 A | 3/1995 | Edwards et al. |
| 5,400,783 A * | 3/1995 | Pomeranz et al. .......... 600/374 |
| 5,401,272 A | 3/1995 | Perkins |
| 5,403,311 A | 4/1995 | Abele et al. |
| 5,409,000 A * | 4/1995 | Imran .......................... 600/374 |
| 5,409,453 A | 4/1995 | Lundquist et al. |
| 5,409,483 A | 4/1995 | Campbell et al. |
| 5,415,657 A | 5/1995 | Taymor-Luia |
| 5,421,819 A | 6/1995 | Edwards et al. |
| 5,423,808 A | 6/1995 | Edwards et al. |
| 5,423,812 A | 6/1995 | Ellman et al. |
| 5,433,739 A | 7/1995 | Sluijter et al. |
| 5,435,805 A | 7/1995 | Edwards |
| 5,441,499 A | 8/1995 | Fritzsch |
| 5,443,470 A | 8/1995 | Stern et al. |
| 5,454,782 A | 10/1995 | Perkins |
| 5,456,662 A | 10/1995 | Edwards et al. |
| 5,456,682 A | 10/1995 | Edwards et al. |
| 5,458,596 A | 10/1995 | Lax et al. |
| 5,458,597 A | 10/1995 | Edwards et al. |
| 5,465,717 A | 11/1995 | Imran et al. |
| 5,470,308 A | 11/1995 | Edwards et al. |
| 5,471,982 A | 12/1995 | Edwards et al. |
| 5,472,441 A | 12/1995 | Edwards et al. |
| 5,484,400 A | 1/1996 | Edwards et al. |
| 5,485,849 A * | 1/1996 | Panescu et al. ............. 600/512 |
| 5,486,161 A | 1/1996 | Lax et al. |
| 5,490,984 A | 2/1996 | Freed |
| 5,496,271 A | 3/1996 | Burton et al. |
| 5,496,311 A | 3/1996 | Abele et al. |
| 5,500,012 A | 3/1996 | Brucker et al. |
| 5,505,728 A | 4/1996 | Ellman et al. |
| 5,505,730 A | 4/1996 | Edwards |
| 5,507,743 A | 4/1996 | Edwards et al. |
| 5,509,419 A | 4/1996 | Edwards et al. |
| 5,514,130 A | 5/1996 | Baker |
| 5,514,131 A | 5/1996 | Edwards et al. |
| 5,520,684 A | 5/1996 | Imran |
| 5,531,676 A | 7/1996 | Edwards et al. |
| 5,531,677 A | 7/1996 | Lundquist et al. |
| 5,536,240 A | 7/1996 | Edwards et al. |
| 5,536,267 A | 7/1996 | Edwards et al. |
| 5,540,655 A | 7/1996 | Edwards et al. |
| 5,549,644 A | 8/1996 | Lundquist et al. |
| 5,554,110 A | 9/1996 | Edwards et al. |
| 5,556,377 A | 9/1996 | Rosen et al. |
| 5,558,672 A | 9/1996 | Edwards et al. |
| 5,558,673 A | 9/1996 | Edwards et al. |
| 5,562,720 A | 10/1996 | Stern et al. |
| 5,571,116 A | 11/1996 | Bolanos et al. |
| 5,578,007 A | 11/1996 | Imran |
| 5,588,432 A | 12/1996 | Crowley |
| 5,588,960 A | 12/1996 | Edwards et al. |
| 5,595,183 A * | 1/1997 | Swanson et al. ............. 600/510 |
| 5,599,345 A | 2/1997 | Edwards et al. |
| 5,609,151 A | 3/1997 | Mulier et al. |
| 5,624,439 A | 4/1997 | Edwards et al. |
| 5,672,153 A | 9/1997 | Lax et al. |
| 5,676,674 A | 10/1997 | Bolanos et al. |
| 5,688,266 A | 11/1997 | Edwards et al. |
| 5,688,490 A | 11/1997 | Tournier et al. |
| 5,702,438 A | 12/1997 | Avitall |
| 5,709,224 A | 1/1998 | Behl et al. |
| 5,732,698 A | 3/1998 | Swanson et al. |
| 5,738,096 A | 4/1998 | Ben-Haim |
| 5,830,213 A | 11/1998 | Panescu et al. |

| | | |
|---|---|---|
| 5,836,874 A | 11/1998 | Swanson et al. |
| 5,860,974 A | 1/1999 | Abele |
| 5,871,483 A | 2/1999 | Jackson et al. |
| 6,006,755 A | 12/1999 | Edwards |
| 6,009,877 A | 1/2000 | Edwards |
| 6,073,052 A * | 6/2000 | Zelickson et al. .......... 607/100 |
| 6,156,032 A * | 12/2000 | Lennox ........................ 606/41 |
| 6,197,022 B1 * | 3/2001 | Baker .......................... 606/33 |

FOREIGN PATENT DOCUMENTS

| | | |
|---|---|---|
| EP | 0 608 609 | 8/1994 |
| WO | 91/01773 | 2/1991 |
| WO | 92/10142 | 6/1992 |
| WO | 93/08755 | 5/1993 |
| WO | 94/10925 | 8/1994 |
| WO | 94/21165 | 9/1994 |
| WO | 94/21178 | 9/1994 |
| WO | 94/22366 | 10/1994 |
| WO | 94/26178 | 11/1994 |
| WO | 95/18575 | 7/1995 |
| WO | 95/19142 | 7/1995 |
| WO | 95/25472 | 9/1995 |
| WO | 96/00042 | 1/1996 |
| WO | 96/16606 | 6/1996 |
| WO | 96/29946 | 10/1996 |
| WO | 97/06857 | 2/1997 |
| WO | 97/32532 | 9/1997 |
| WO | 97/43971 | 11/1997 |

OTHER PUBLICATIONS

Dallemagne, B. et al., "Laparoscopic Nissen Fundoplication: Preliminary." Surgical Laparoscopy & Endoscopy. 1991 1(3): 138–43.

Hinder, R.A. et al., "The Technique of Laparoscopic Nissen Fundoplication." Surgical Laparoscopy & Endoscopy. 1992. 2(3): 265–272.

Karlstrom, L.H. et al. "Ectopic jejunal pacemakers and enterogastric reflux after Roux gastrectomy: Effect of intestinal pacing." Surgery 1989. 106(3): 486–495.

Kelly, KA. et al., "Doudenal–gastric reflux and slowed gastric emptying by electrical pacing of the canine duodenal pacesetter potential." Gastroenterology. 1977. 72(3): 429–33.

Reynolds, J.C. "Influence of pathophysiology, severity, and cost on the medical management of gastroesophageal reflux disease." Am J Health–Syst Pharm. 53 (22 Suppl 3): 55–12.

Urschel, J.D. "Complications of Antireflux Surgery." Am J Surg. 1993. 166(1): 68–70.

Kaneko, et al., Physiological Laryngeal Pacemaker, May 1985, Trans Am Soc. Artif. Intern Organs, vol. XXXI, pp. 293–296.

Mugica et al. Direct Diaphragm Stimulation, Jan. 1987 PACE, vol. 10, pp. 252–256.

Mugica et al., Neurostimulation: An Overview, Chapter 21, Preliminary Test of a Muscular Diaphragm pacing System on Human Patients. 1985. pp. 3. 263–279.

Rice et al., Endoscopic Paranasal Sinus Surgery, Chapter 5, Functional Endoscopic Paranasal Sinus Surgery, The Technique of Messerklinger, Raven Press, 1988, pp. 75–104.

Rice et al., Endoscopic Paranasal Sinus Surgery, Chapter 6, Total Endoscopic Sphenoethmoidectomy, The Technique of Wigand, Raven Press, 1988, pp. 105–125.

* cited by examiner

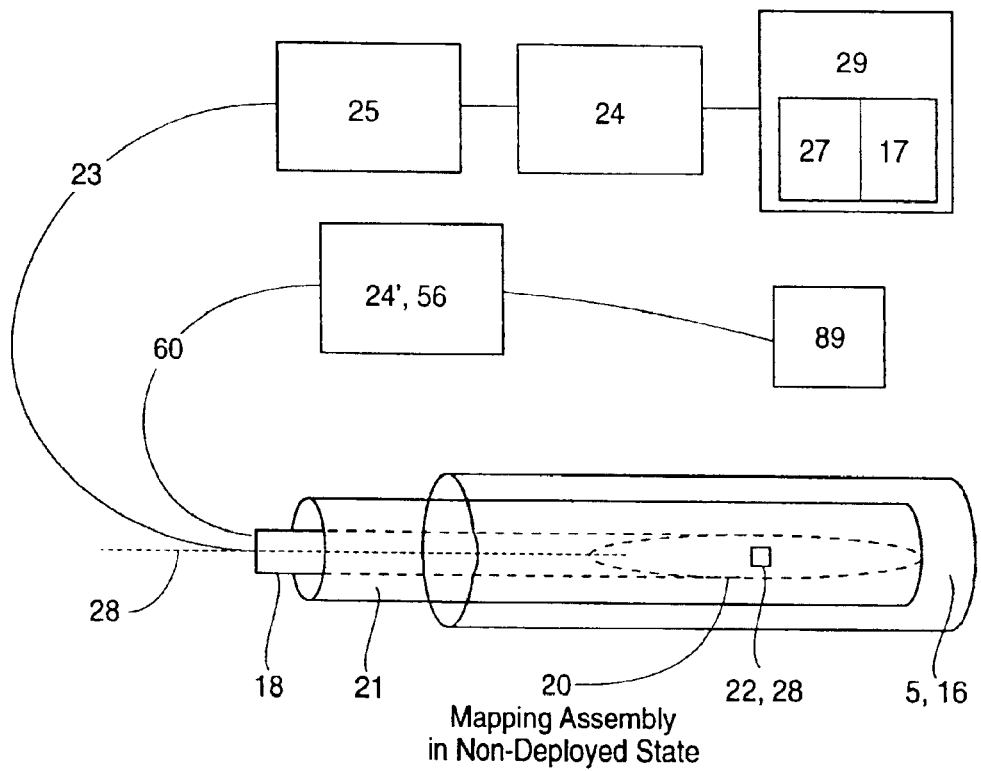
Fig. 2b
Mapping Assembly
in Non-Deployed State
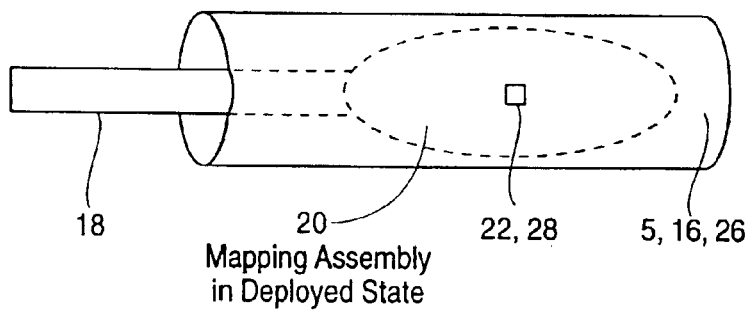
Mapping Assembly
in Deployed State

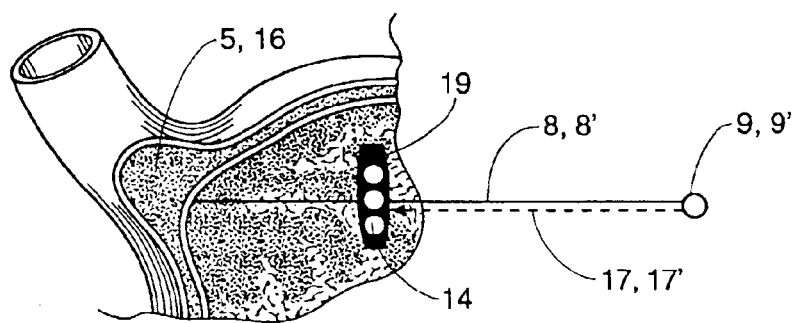
Fig. 25e
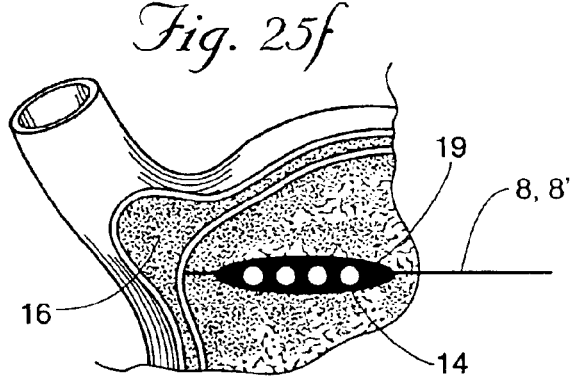
Fig. 25f
Fig. 25g
Shapes of Areas of Electrical Blockage
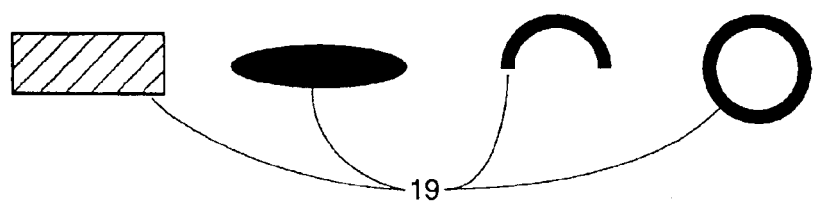

METHOD TO TREAT GASTRIC REFLUX VIA THE DETECTION AND ABLATION OF GASTRO-ESOPHAGEAL NERVES AND RECEPTORS

CROSS-RELATED APPLICATIONS

This application is a continuation of U.S. patent application Ser. No. 09/410,448, filed Oct. 1, 1999, now U.S. Pat. No. 6,405,732 and entitled "Method to Treat Gastric Reflux via the Detection and Ablation of Gastro-Esophageal Nerves and Receptors," which is a continuation-in-part of U.S. patent application Ser. No. 09/026,086 filed Feb. 19, 1998, now U.S. Pat. No. 6,006,755, and is related to U.S. patent application Ser. No. 09/007,238, filed Jan. 14, 1998, now abandoned all of which are incorporated by reference.

BACKGROUND OF THE INVENTION

1. Field of the Invention

This invention relates generally to a method to treat gastroesophageal reflux, and more particularly the detection and ablation and/or necrosis of gastroesophageal nerves and receptors causing transient relaxation of the lower esophageal sphincter and gastroesophageal reflux.

2. Description of Related Art

Gastroesophageal reflux disease (GERD) is a common gastroesophageal disorder in which the stomach contents are ejected into the lower esophagus due to a dysfunction of the lower esophageal sphincter (LES). These contents are highly acidic and potentially injurious to the esophagus resulting in a number of possible complications of varying medical severity. The reported incidence of GERD in the U.S. is as high as 10% of the population (Castell D O; Johnston B T: *Gastroesophageal Reflux Disease: Current Strategies For Patient Management.* Arch Fam Med, 5(4):221–7; (1996 April)).

Acute symptoms of GERD include heartburn, pulmonary disorders and chest pain. On a chronic basis, GERD subjects the esophagus to ulcer formation, or esophagitis and may result in more severe complications including esophageal obstruction, significant blood loss and perforation of the esophagus. Severe esophageal ulcerations occur in 20–30% of patients over age 65. Moreover, GERD causes adenocarcinoma, or cancer of the esophagus, which is increasing in incidence faster than any other cancer (Reynolds J C: *Influence Of Pathophysiology, Severity, And Cost On The Medical Management Of Gastroesophageal Reflux Disease.* Am J Health Syst Pharm, 53(22 Suppl 3):S5–12 (1996 Nov. 15)).

The lower esophageal sphincter is a thickened ring of smooth muscle at the lower end of the esophagus. Normally, the LES is in a state of contraction and functions to keep the acid contents of the stomach from refluxing into the esophagus. In a healthy person the muscle relaxes only during swallowing to allow food to pass and also on average three to four times and hour in phenomenon known as transient lower esophageal sphincter relaxation (TLESR). In a person suffering from GERD, the frequency of TLSER is much higher rising as high as eight or more times and hour.

Since the resting tone of the LES is maintained by both myogenic (muscular) and neurogenic (nerve) mechanisms, some believe that abnormal or aberrant electrical signals in the lower esophageal sphincter or surrounding region of the stomach including the cardia can cause the sphincter to spontaneously relax. Such signals may cause a higher than normal frequency of TLESRs allowing acidic stomach contents to be repeatedly ejected into the esophagus and cause the complications described above. Research has shown that unnatural electrical signals in the stomach and intestine can cause reflux events in those organs (Kelly K A, et al: *Duodenal-gastric Reflux and Slowed Gastric Emptying by Electrical Pacing of the Canine Duodenal Pacesetter Potential.* Gastroenterology. 1977 March; 72(3): 429–433). In particular, medical research has found that sites of aberrant electrical activity or electrical foci may be responsible for those signals (Karlstrom L H, et al: *Ectopic Jejunal Pacemakers and Enterogastric Reflux after Roux Gastrectomy: Effect Intestinal Pacing.* Surgery. 1989 September; 106(3): 486–495). Similar aberrant electrical sites in the heart, which cause contractions of the heart muscle to take on life threatening patterns or dysrhythmias, can be identified and treated using mapping and ablation devices as described in U.S. Pat. No. 5,509,419. However, there is no current device or associated medical procedure available for the electrical mapping and treatment of aberrant electrical sites in the LES and stomach as a means for treating GERD.

GERD is believed to be caused by a combination of conditions that increase the presence of acid reflux in the esophagus. These conditions include transient LES relaxation, decreased LES resting tone, impaired esophageal clearance, delayed gastric emptying, decreased salivation, and impaired tissue resistance.

Current drug therapy for GERD includes histamine receptor blockers which reduce stomach acid secretion and other drugs which may completely block stomach acid. However, while pharmacologic agents may provide short term relief, they do not address the underlying cause of LES dysfunction.

Invasive procedures requiring percutaneous introduction of instrumentation into the abdomen exist for the surgical correction of GERD. One such procedure, Nissen fundoplication, involves constructing a new "valve" to support the LES by wrapping the gastric fundus around the lower esophagus. Although the operation has a high rate of success, it is an open abdominal procedure with the usual risks of abdominal surgery including: postoperative infection, herniation at the operative site, internal hemorrhage and perforation of the esophagus or of the cardia. In fact, a recent 10 year, 344 patient study reported the morbidity rate for this procedure to be 17% and mortality 1% (Urschel, J D: *Complications Of Antireflux Surgery*, Am J Surg 166(1): 68–70; (1993 July)). This rate of complication drives up both the medical cost and convalescence period for the procedure and may exclude portions of certain patient populations (e.g., the elderly and immuno-compromised).

Efforts to perform Nissen fundoplication by less invasive techniques have resulted in the development of laparoscopic Nissen fundoplication. Laparoscopic Nissen fundoplication, reported by Dallemagne et al. *Surgical Laparoscopy and Endoscopy*, Vol. 1, No. 3, (1991), pp. 138–43 and by Hindler et al. *Surgical Laparoscopy and Endoscopy*, Vol. 2, No. 3, (1992), pp. 265–272, involves essentially the same steps as Nissen fundoplication with the exception that surgical manipulation is performed through a plurality of surgical cannula introduced using trocars inserted at various positions in the abdomen.

Another attempt to perform fundoplication by a less invasive technique is reported in U.S. Pat. No. 5,088,979. In this procedure an invagination device containing a plurality of needles is inserted transorally into the esophagus with the needles in a retracted position. The needles are extended to engage the esophagus and fold the attached esophagus beyond the gastroesophageal junction. A remotely operated stapling device, introduced percutaneously through an operating channel in the stomach wall, is actuated to fasten the invaginated gastroesophageal junction to the surrounding involuted stomach wall.

Yet another attempt to perform fundoplication by a less invasive technique is reported in U.S. Pat. No. 5,676,674. In this procedure, invagination is done by a jaw-like device and fastening of the invaginated gastroesophageal junction to the fundus of the stomach is done via a transoral approach using a remotely operated fastening device, eliminating the need for an abdominal incision. However, this procedure is still traumatic to the LES and presents the postoperative risks of gastroesophageal leaks, infection and foreign body reaction, the latter two sequela resulting when foreign materials such as surgical staples are implanted in the body.

While the methods reported above are less invasive than an open Nissen fundoplication, some still involve making an incision into the abdomen and hence the increased morbidity and mortality risks and convalescence period associated with abdominal surgery. Others incur the increased risk of infection associated with placing foreign materials into the body. All involve trauma to the LES and the risk of leaks developing at the newly created gastroesophageal junction. None provide a means for detecting and treating aberrant electrical sites causing abnormal LES relaxation and gastroesophageal reflux.

There is a need to provide a method to detect and treat aberrant bioelectric activity of a sphincter and/or a stomach including myoelectric activity. There is another need to provide a method to detect and treat an electrical foci of the aberrant bioelectric activity of a sphincter and/or a stomach. There is a further need to detect and treat an electrically conductive pathway of the aberrant bioelectric activity of a sphincter and/or a stomach.

SUMMARY OF THE INVENTION

Accordingly, an object of the invention is to provide a method to diagnose and treat sphincters and/or a stomach.

Another object of the invention is to provide a method to diagnose and treat gastroesophageal reflux disease.

A further object of the invention is to provide a method to detect and treat bioelectrical activity of a sphincter and/or a stomach causing transient relaxation of the lower esophageal sphincter.

Yet another object of the invention is to provide a method to detect and treat electrically conductive pathways of bioelectrical activity in a sphincter and/or a stomach causing transient relaxation of the lower esophageal sphincter.

Still a further object of the invention is to provide a method to detect and treat a nerve pathway in a sphincter and/or a stomach causing transient relaxation of the lower esophageal sphincter.

Another object of the invention is to provide a method to detect and treat a nerve pathway in a sphincter and/or a stomach causing transient relaxation of the lower esophageal sphincter while preserving a swallowing reflex A further object of the invention is to provide a method to detect and treat a receptor pathway in a sphincter and/or a stomach causing transient relaxation of the lower esophageal sphincter.

Yet a further object of the invention is to provide a method to create an area of electrical block to bioelectric activity of the lower esophageal sphincter and/or stomach causing transient relaxation of the lower esophageal sphincter.

These and other objects of the invention are provided in a method of treating a sphincter that provides a sphincter electropotential mapping device with at least one of a mapping electrode or a treatment electrode. The sphincter electropotential mapping device is introduced into at least a portion of the sphincter, the lower esophageal sphincter, stomach, the cardia or the fundus. Bioelectric activity causing a relaxation of the sphincter is detected and energy is delivered from either the mapping electrode or the treatment electrode to treat the bioelectric activity.

In another embodiment, a method of treating a sphincter that provides a sphincter electropotential mapping device with at least one of a mapping electrode or a treatment electrode. The sphincter electropotential mapping device is introduced into at least a portion of the sphincter, the lower esophageal sphincter, stomach, the cardia or the fundus. The sphincter, lower esophageal sphincter, stomach, cardia or fundus is stimulated to produce a transient relaxation of the sphincter. The portion of the sphincter, lower esophageal sphincter, stomach, cardia or fundus causing a relaxation of the sphincter is indentified. Energy is delivered from the sphincter electropotential mapping device to treat the portion the sphincter, lower esophageal sphincter, stomach, cardia or fundus causing the transient relaxation of the sphincter.

BRIEF DESCRIPTION OF THE DRAWINGS

FIG. 2B is a lateral view of an apparatus, useful with the method of the present invention, illustrating the energy delivery device, power source, controllers, map, display device, and the mapping assembly in an expanded and contracted state.

FIGS. 25E–F are lateral views of the sphincter wall illustrating the use of lesions to create an area of electrical block to bioelectrical signals including those causing TLSERS.

FIG. 25G is a lateral view of the stomach illustrating the various shapes of areas of electrical block to bioelectrical signals.

DETAILED DESCRIPTION

Figure 1:
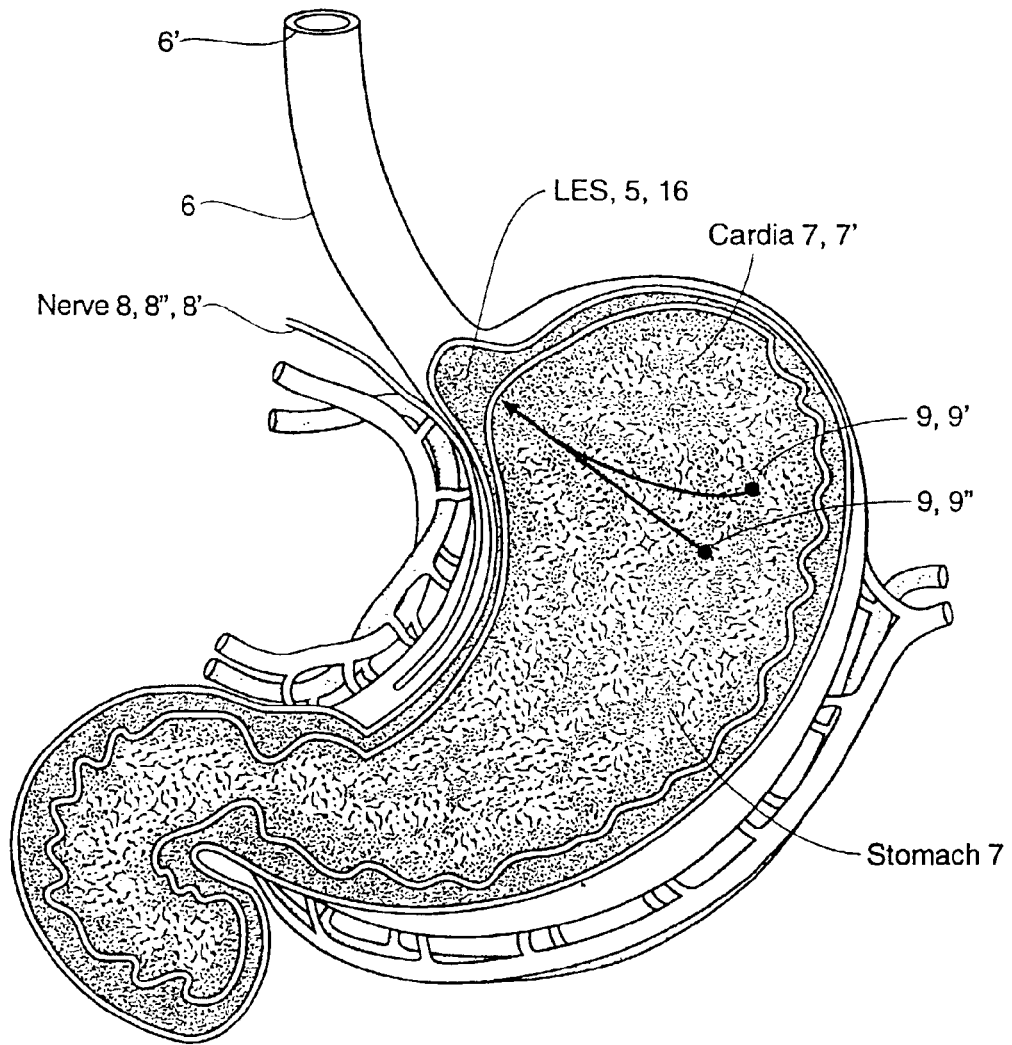
FIG. 1 is an illustrated lateral view of the upper GI tract including the esophagus and lower esophageal sphincter, cardia and fundus.

FIG. 1 depicts the anatomy of the lower esophageal sphincter (LES) 5 and surrounding structures. The LES 5 consists of a thickened ring-like structure of smooth muscle at the junction between the esophagus 6 and the stomach 7. The muscles of the LES 5 consist of both circumferential and longitudinal oriented muscle. Normally, the LES 5 is in a state of contraction, and functions to keep the acidic contents of the stomach from refluxing into the esophagus (via the generation of a pressure of 20–30 mm hg over stomach pressure). However during swallowing and also every three to four times and hour the LES relaxes for several seconds or longer in a phenomena known as transient lower esophageal sphincter relaxation (TLESR). In a person suffering from GERD, the frequency of TLSER is much higher rising as high as eight or more times in an hour.

The LES 5 is enervated with autonomic nerve fibers 8 that perform several functions. These include maintaining a resting tone to keep the LES in a state of contraction; and relaxing the LES to allow swallowing, accommodate pressure increases in the stomach and a to initiate TLESRs. The nerve fibers include efferent fibers 8" going from the brain and/or the upper esophagus 6' to the LES and afferent fibers 8' going from portions of the stomach to the LES as well as from the LES to the brain. Efferent fibers 8" include vagus nerves, while afferent nerve fibers 8' include those leading from gastric receptors 9 such as the mechanoreceptors 9' and chemoreceptors 9" through the cardia 7' to the LES. Stimulation from one or both of these receptors 9, (due to stretching of stomach from ingested food, or a change in stomach pH) is thought to be a possible cause of LES relaxation. Therefore one embodiment of the invention described herein for treating GERD involves the ablation and/or electrical block of the nerve fibers and or pathways leading from gastric receptors 9 including the mechanoreptors 9' and chemoreptors 9" to the LES 5. In various embodiments, the blockage can be achieve by ablating the fibers 8 and/or receptors 9 via the application of heat and/or ablative agents (e.g. ethanol, quinolinic acid, glutamate, botoxin or other neurotoxin known in the art) to attenuate and/or eliminate the nerve impulse going from these receptors to the LES or surrounding structures. The electrical block or ablation can be done anywhere along the pathway from the receptor to the LES but in a preferred embodiment, the ablation is done in or near the cardia and/or LES. In various embodiments, the block is achieved by the delivery of energy in the form of heat to create lesions at or near the desired nerve pathway or receptor. In embodiments using electromagnetic energy (eg. electrical, RF and the like) described herein, the nerve pathway itself can be used as conduit to deliver ablative energy to the target treatment site. In various embodiments, the block can be achieved without injury of or damage of nerves involved in the swallowing reflex including the vagus and other efferent nerves 8". This can be achieved via the use of cooling and other means described herein. In another embodiment, this is accomplished through the use of a signal stimulation device/means described here in, to induce and monitor the presence of the swallowing reflex before during or after the delivery of energy to the treatment site 12.

Figure 2A:
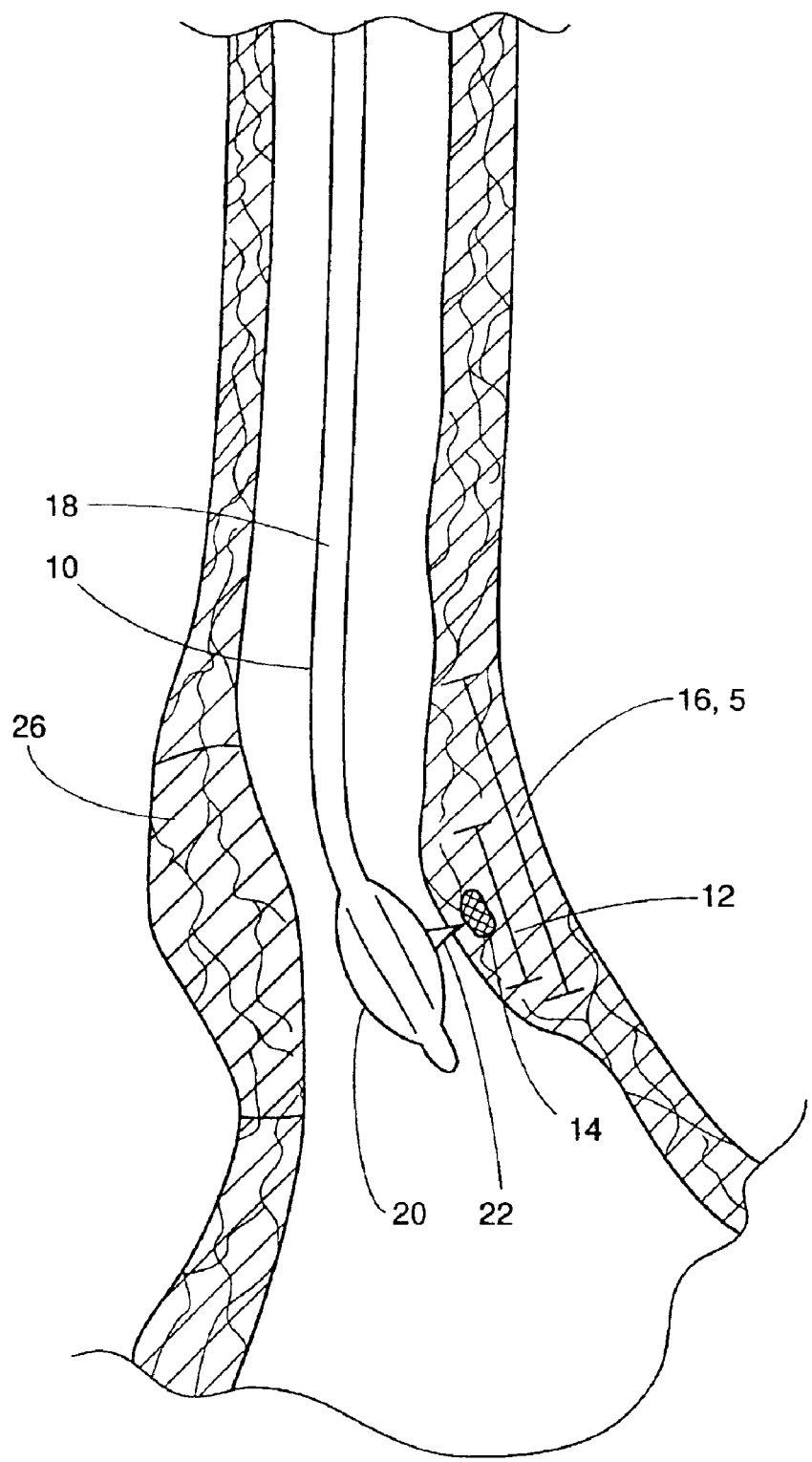
FIG. 2A is an illustrated lateral view of the upper GI tract including the esophagus and lower esophageal sphincter and the positioning of the sphincter mapping and treatment apparatus in an embodiment of the method of the present invention.

FIG. 2A depicts one embodiment of a sphincter mapping and treatment apparatus 10 that is used to both map and treat gastric bioelectric activity causing transient relaxation of the sphincter and subsequent gastroesophageal reflux. Specifically, apparatus 10 delivers energy to a treatment site 12 to produce lesions 14 in a sphincter 16, such as the lower esophageal sphincter 5. Apparatus 10 comprises a flexible elongated shaft 18, also called shaft 18 or catheter 18, coupled to an expandable mapping assembly 20, in turn coupled with one or more mapping electrodes 22 which can also serve as treatment electrodes 22 capable of delivering energy to treatment site 12.

Expandable mapping assembly 20 establishes a three dimensional array of mapping electrodes 22. In use, the expandable mapping assembly 20 records the activation times, the distribution, and the waveforms of the myoelectric or neuroelectric action potentials in sphincter 16, such as the LES 5 and adjoining structures that trigger aberrant and/or transient relaxation of smooth muscle tissue in the sphincter or LES. Suitable materials for mapping electrodes 22 include gold, platinum, silver, copper and alloys and combinations thereof, as well as other conductors known to those skilled in the art.

Referring now to FIG. 2*a* and FIG. 2*b*, mapping electrodes 22 are configured to be coupled to a controller 24. Controller 24 receives and processes the potentials recorded by the mapping electrodes 22 on expandable mapping assembly 20 and produces an electropotential map 27, also called a map 27, of the bioelectric signals 17, including myoelectric and neuroelectric signals 17, in sphincter 16. Controller 24 and electropotential map 27 are used by the physician to diagnose abnormalities and pathologies within sphincter 16 and adjoining structures which will be further discussed herein. Controller 24 can be coupled to an output or display device 29 that can include a cathode ray tube, liquid crystal display, passive or active matrix flat screen display or printer and the like.

Myoelectric and neuroelectric signals 17 can include nerve action potentials: both efferent and afferent; and depolarization signals in smooth and skeletal muscle.

Expandable mapping assembly 20 has a central longitudinal axis 28 and is moveable between contracted and expanded positions substantially there along. This can be accomplished by a ratchet mechanism and the like as is known to those skilled in the art and by the use of other mechanisms disclosed herein. The expandable mapping assembly 20 is further configured to be positionable in a sphincter 16 such as the LES or adjacent anatomical structure, such as the cardia 7' of the stomach. Once positioned within the desired sphincter 16, the operating physician causes expandable mapping assembly 20 to expand to an expanded stationary position within the sphincter so that mapping electrodes 22 thereof engage sphincter wall 26 for sensing and detecting electrical energy or impulses therefrom. At least portions of sphincter mapping and treatment apparatus 10 may be sufficiently radiopaque in order to be visible under fluoroscopy and/or sufficiently echogenic to be visible under ultrasonography. Also, as will be discussed herein, sphincter mapping and treatment apparatus 10 can include visualization capability including, but not limited to, a viewing scope, an expanded eyepiece, fiber optics, video imaging and the like.

Referring now to FIG. 2B, shaft 18 is configured to be coupled to expandable mapping assembly 20 and has sufficient length to position expandable mapping assembly 20 in the LES and/or stomach using a transoral approach. Typical lengths for shaft 18 include, but are not limited to, a range of 40–180 cm. In various embodiments, shaft 18 is flexible, articulated and steerable and can contain fiber optics (including illumination and imaging fibers), fluid and gas paths, and sensor and electronic cabling. In one embodiment, shaft 18 can be a multi-lumen catheter, as is well known to those skilled in the art.

In another embodiment of the invention, an introducing member 21, also called an introducer, is used to introduce sphincter mapping and treatment apparatus 10 into the LES including transoral introduction through the mouth and the throat. Introducer 21 can also function as a sheath for expandable mapping assembly 20 to keep it in a nondeployed or contracted state during introduction into the LES. In various embodiments, introducer 21 is flexible, articulated and steerable, and contains a continuous lumen of sufficient diameter to allow the advancement of sphincter mapping and treatment apparatus 10 within. Typical diameters for introducer 21 include 0.1 to 2 inches, while typical length include 40–180 cm. Suitable materials for introducer 21 include wire-reinforced plastic tubing as is well known to those skilled in the art. Alternatively, the catheter 18 may be deployed over a guide wire through the patient's mouth and pharynx, and into the esophagus without use of an introducer 21. Still alternatively, catheter 18 may be passed through the patient's mouth and pharynx, and into the esophagus without use of either a guide wire or introducer.

Figure 3:
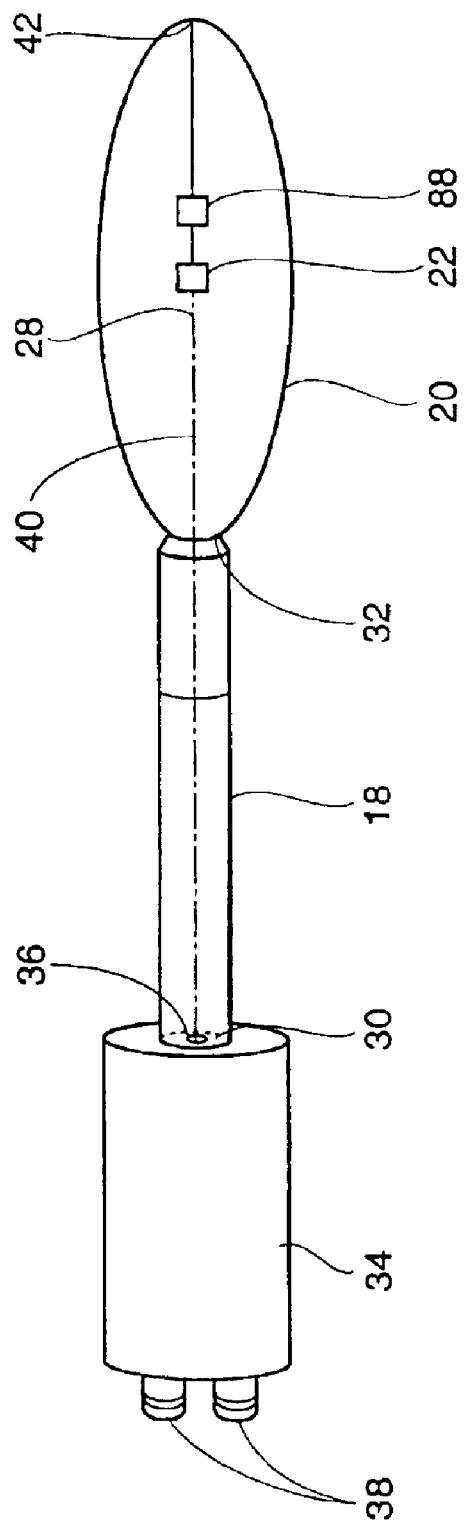
FIG. 3 depicts a lateral view of an apparatus, useful with the method of the present invention that illustrates components on the flexible shaft including a proximal fitting, connections and proximal and distal shaft segments.
Figure 4A:
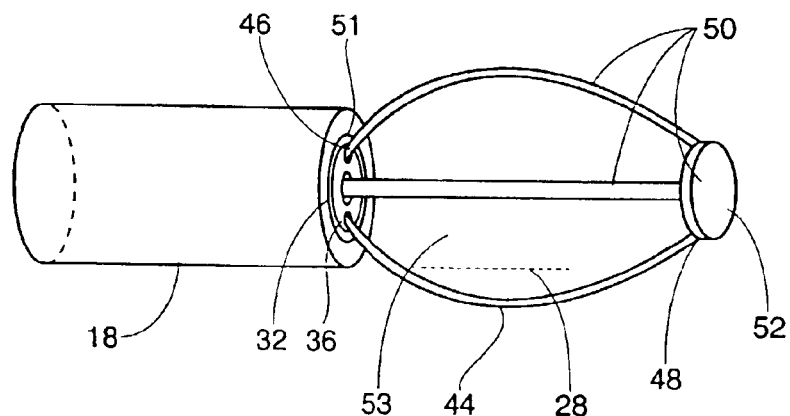
FIG. 4A illustrates a lateral view of the basket assembly used in an embodiment of the method of the present invention.
Figure 4B:
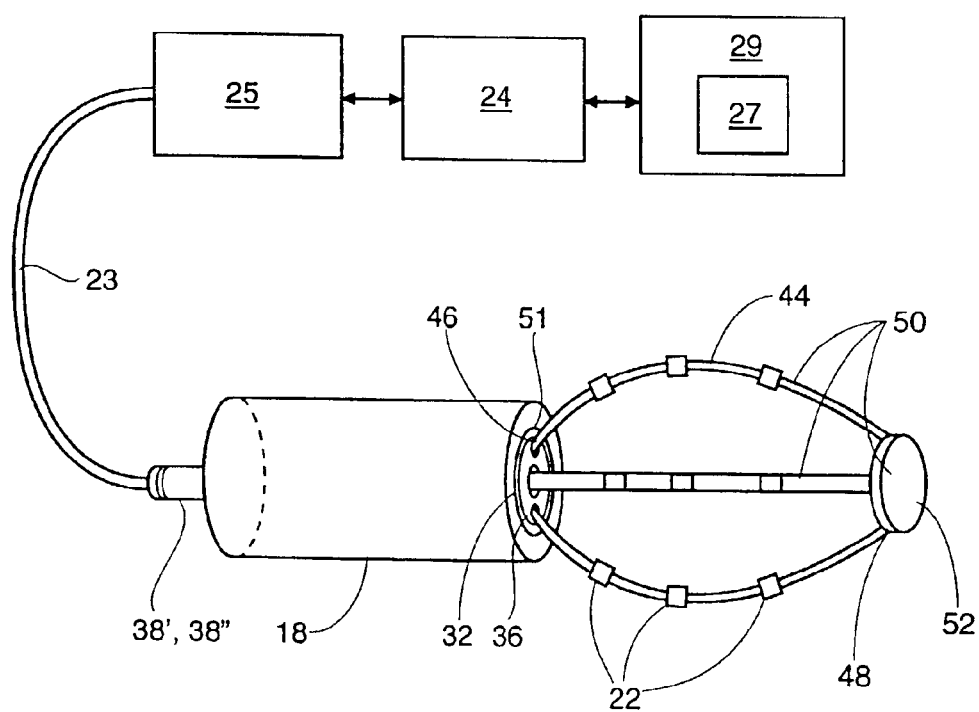
FIG. 4B is a lateral view that illustrates placement of the mapping electrodes on the basket assembly and their electrical connections to the controller.

Referring now to FIGS. 3, 4A and 4B, the flexible elongate shaft 18 is circular in cross section and has proximal and distal extremities (also called ends) 30 and 32. Shaft 18 may also be coupled at its proximal end 30 to a proximal fitting 34, also called a handle, used by the physician to manipulate sphincter mapping and treatment apparatus 10 to reach treatment site 12. Shaft 18 may have one or more shaft lumens 36 that extend the full length of shaft 18, or part way from shaft proximal end 30 to shaft distal end 32. Shaft lumens 36 may be used as paths for catheters, guide wires, pull wires, insulated wires and cabling, fluid and optical fibers. Shaft lumens 36 are connected to and/or accessed by connections 38, also called connector 38, on or adjacent to proximal fitting 34. Connections 38 can include luer-lock, swage and other mechanical varieties well known to those skilled in the art. Connections 38 can also include electrical connections 38' which can include lemo-connectors, micro connectors and other electrical varieties well known to those skilled in the art. Additionally, connectors 38 can include opto-electronic connections 38" which allow optical and electronic coupling of optical fibers and/or viewing scopes to illuminating sources, eye pieces, video monitors and the like. In various embodiments, shaft 18 may stop at the proximal extremity 40 of expandable mapping assembly 20 or extend to, or past, the distal extremity 42 of expandable mapping assembly 20. Suitable materials for shaft 18 include, but are not limited to, polyethylenes, polyurethanes, Pebax®, polyimides, nylons, copolymers thereof and other medical plastics known to those skilled in the art.

Referring now to FIG. 4A, in one embodiment of the present invention, expandable mapping assembly 20 comprises one or more elongated arms 44 that are joined at their proximal arm ends 46 and distal arm ends 48 to form a basket assembly 50. Proximal arm end 46 is attached to a supporting structure, which can be the distal end 32 of shaft 18 or a proximal cap 51. Likewise, distal arm end 48 is also attached to a supporting structure which can be a distal basket cap 52 or shaft 18. Attached arms 44 may form a variety of geometric shapes including, but not limited to, curved, rectangular, trapezoidal and triangular. Arms 44 can have a variety of cross sectional geometries including, but not limited to, circular, rectangular and crescent-shaped. Also, arms 44 are of a sufficient number (two or more), and have sufficient spring force (0.01 to 0.5 lbs. force ) so as to collectively exert adequate force on sphincter wall 26 to sufficiently open and efface the folds of sphincter 16 to allow treatment with sphincter mapping and treatment apparatus 10, while preventing herniation of sphincter wall 26 into the spaces 53 between arms 44. Suitable materials for arms 44 include, but are not limited to, spring steel, stainless steel, superelastic shape memory metals such as nitinol or wire-reinforced plastic tubing as is well known to those skilled in the art. Also, arms 44 can be configured to have a selectable spring constant for parallel or perpendicular deflection to the longitudinal axis 28 of arm 44.

Referring now to FIG. 4B, a plurality of spaced apart mapping electrodes 22 are carried by each arm 44 for engaging sphincter wall 26 and are electrically coupled by a conductor 23 to a multiplexer chip 25 for transmitting signals sensed thereby to controller 24 via electrical connections 38'. Various geometric patterns for placement of mapping electrodes 22 on basket assembly 50 or expandable mapping assembly 20 are disclosed later herein. Multiplexor chip 25 transmits only a selected one of the electrode signals at a time to the controller 24, subject to switching signals that controller 24 generates. The switching signals of controller 24 serve to multiplex the electrode signals through electrical connector 38'. This reduces the number of electrical pathways required through shaft lumen 36. In various embodiments, conductor 23 can be an insulated lead wire as is well known to those skilled in the art.

In various embodiments, expandable mapping assembly 20 or basket assembly 50 may also be coupled to one or more energy delivery devices 88, also called electrodes, coupled to power source 56. Energy delivery devices 88 are used to delivery energy to treatment site 12 to produce lesions 14. Expandable mapping assembly 20 is further configured to facilitate the positioning of energy delivery devices 88, to a selectable depth in a sphincter wall 26 or adjoining anatomical structure. In one embodiment mapping electrodes 22 can also be used as energy delivery devices.

Figure 5A:
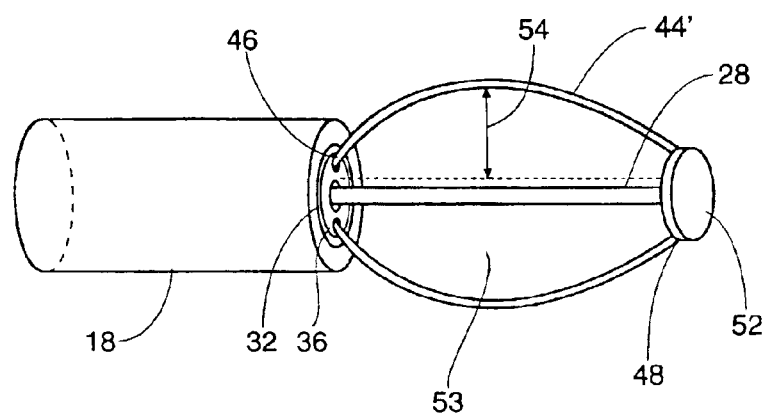
FIG. 5A is a lateral view of the basket assembly that illustrates the range of camber in the basket assembly.

Referring to FIG. 5A, arms 44 can have an outwardly bowed shaped memory for expanding the basket assembly into engagement with sphincter wall 26 with the amount of bowing, or camber 54 being selectable from a range 0 to 2 inches from longitudinal axis 28 of basket assembly 50. For the case of a curve-shaped arm 44', expanded arms 44' are circumferentially and symmetrically spaced-apart.

Figure 5B:
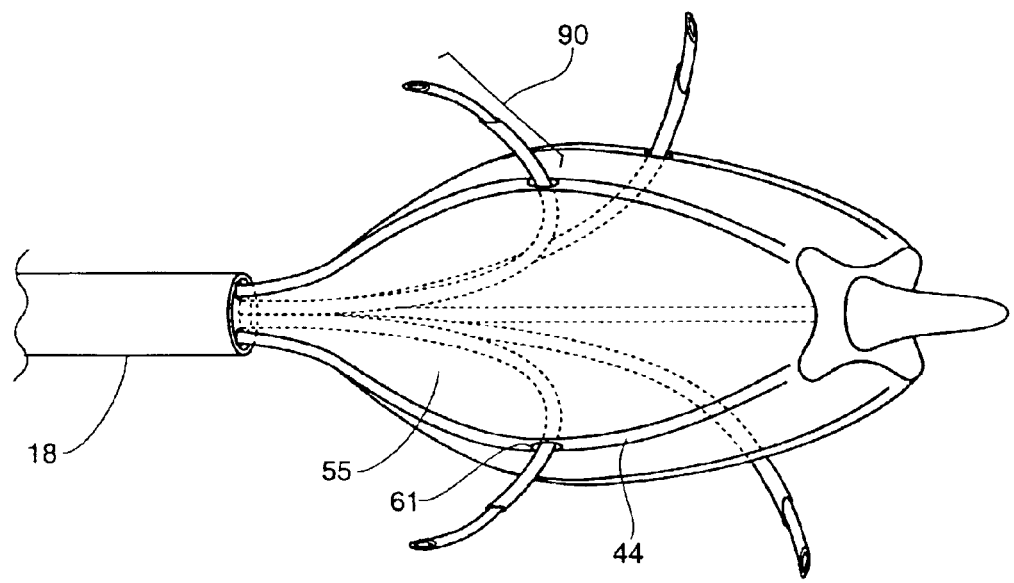
FIG. 5B is a perspective view illustrating a balloon coupled to the basket assembly.

In another embodiment shown in FIG 5B, an expansion device 55, which can be a balloon, is coupled to an interior or exterior of basket assembly 50. Balloon 55 is also coupled to and inflated by shaft lumen 36 using gas or liquid. In various other embodiments (not shown), arms 44 may be asymmetrically spaced and/or distributed on an arc less than 360. Also, arms 44 may be preshaped at time of manufacture or shaped by the physician.

Figure 6A:
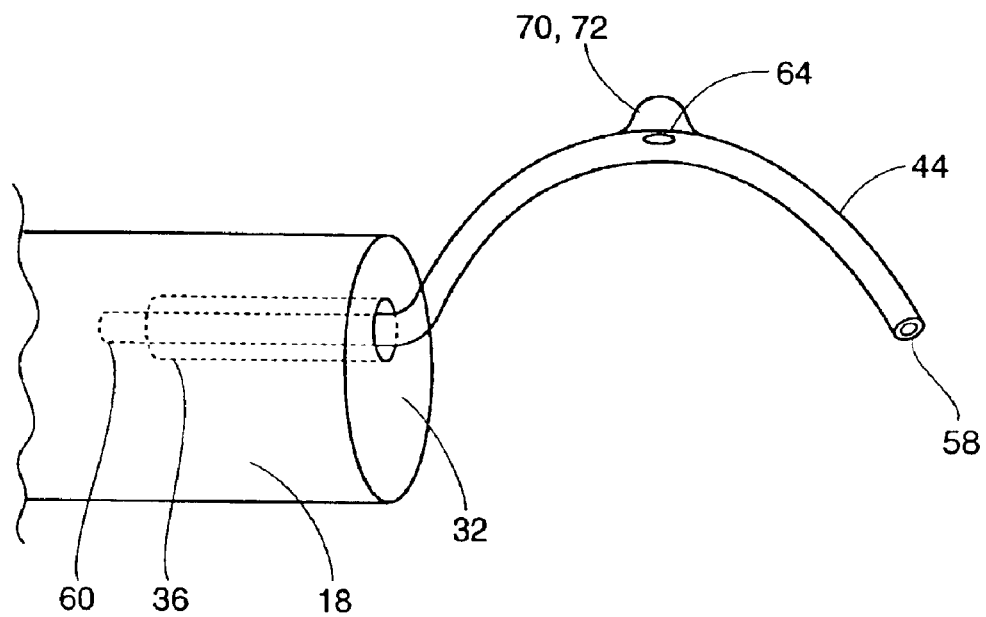
FIG. 6A is a lateral view of the junction between the basket arms and the shaft illustrating the pathway used for advancement of a movable wire or the delivery of fluids.
Figure 6B:
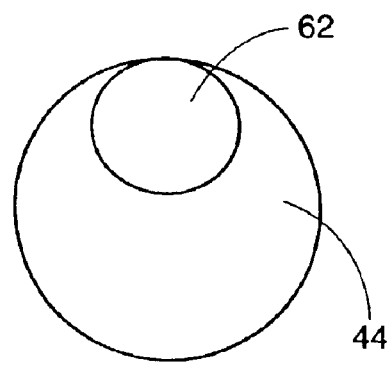
FIG. 6B is a frontal view of a basket arm in an alternative embodiment of an apparatus, useful with the method of the present invention, illustrating a track in the arm used to advance the movable wire.
Figure 7:
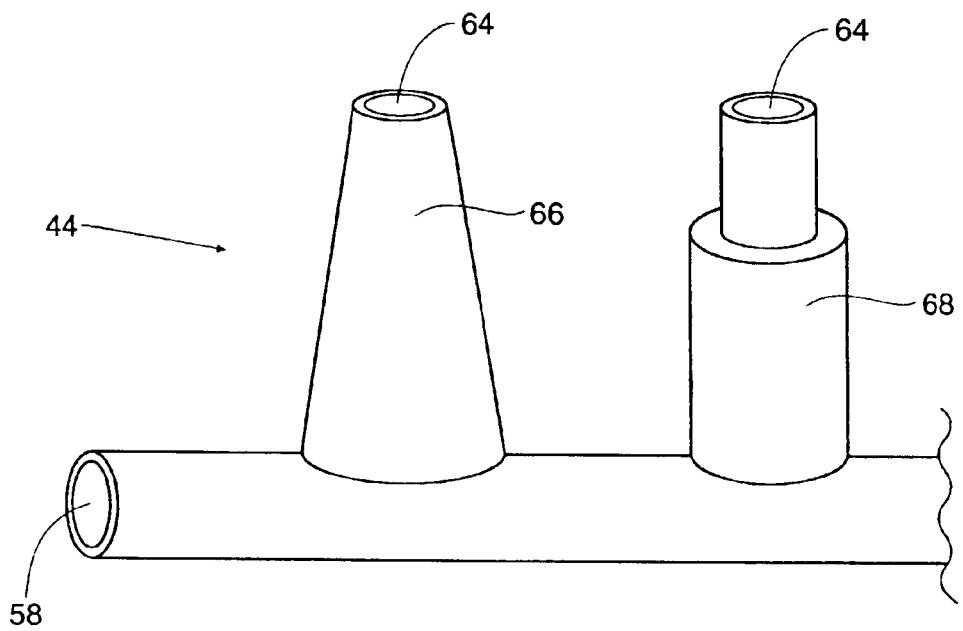
FIG. 7 is a cross-sectional view of a section of the basket arm illustrating stepped and tapered sections in basket arm apertures.

Referring now to FIG. 6A, arms 44 may also be solid or hollow with a continuous lumen 58 that may be coupled with shaft lumens 36. These coupled lumens provide a path for the delivery of a fluid or electrode delivery member 60 from shaft 18 to any point on expandable mapping assembly 20. In various embodiments electrode delivery member 60 can be an insulated wire, an insulated guide wire, a plastic-coated stainless steel hypotube with internal wiring or a plastic catheter with internal wiring, all of which are known to those skilled in the art. As shown in FIG. 6B, arms 44 may also have a partially open channel 62, also called a track 62, that functions as a guide track for electrode delivery member 60. Referring back to FIG. 6A, arms 44 may have one or more apertures 64 at any point along their length that permit the controlled placement of electrodes 88 at or into sphincter wall 26. Referring now to FIG. 7, apertures 64 may have tapered sections 66 or stepped sections 68 in all or part of their length, that are used to control the penetration depth of electrodes 88 into sphincter wall 26. Referring back to FIG. 6A, apertures 64 in combination with arm lumens 58 and shaft lumens 36 may be used for the delivery of a cooling solution 70 or electrolytic solution 72 to treatment site 12 as described herein. Additionally, arms 44 can also carry a plurality of longitudinally or radially spaced apart radiopaque and or echogenic markers or traces, not shown in the drawings, formed of suitable materials to permit viewing of basket assembly 50 via fluoroscopy, ultrasonography and the like. Suitable radiopaque materials include platinum or gold, while suitable echogenic materials include gas filled micro-particles as described in U.S. Pat. Nos. 5,688,490 and 5,205,287. Arms 44 may also be color-coded to facilitate their identification via visual medical imaging methods and equipment, such as endoscopic methods, which are well known to those skilled in the art.

Figure 8:
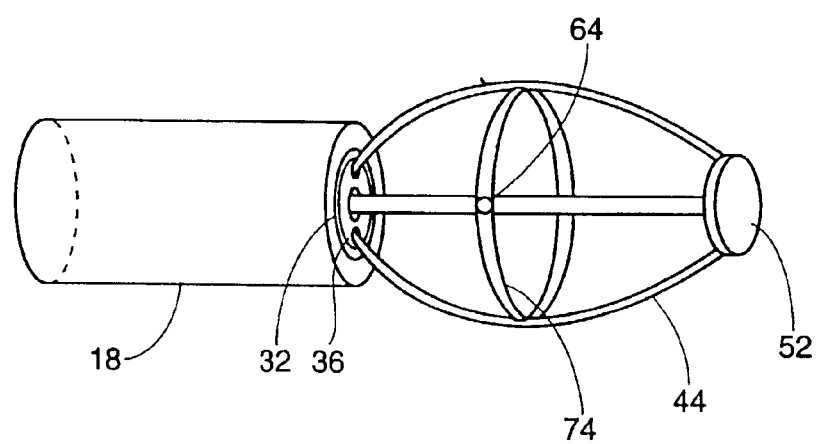
FIG. 8 is a lateral view of the basket assembly illustrating the placement of the radial supporting member.

In another embodiment of the present invention, a radial supporting member 74 (also called a strut 74) is attached to two or more arms 44. Radial supporting member 74 can be attached to arms 44 along a circumference of basket assembly 50 as shown in FIG. 8. Apertures 64 can extend through radial supporting member 74 in one or more places. Radial supporting member 74 serves the following functions: i) facilitates opening and effacement of the folds of sphincter 16, ii) enhances contact of apertures 64 with sphincter wall 26; and iii) reduces or prevents the tendency of arms 44 to bunch up. The cross sectional geometry of radial supporting member 74 can be rectangular or circular, though it will be appreciated that other geometries are equally suitable.

Figure 9A:
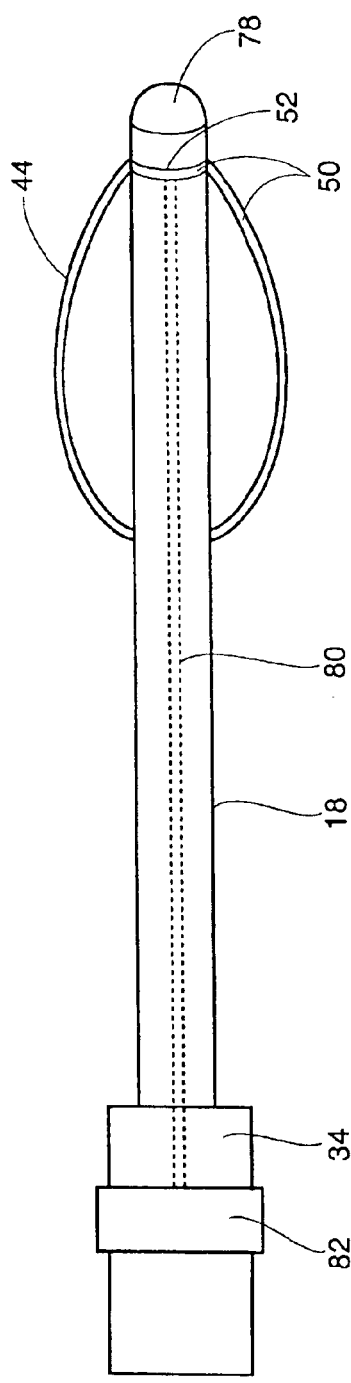
FIG. 9A is a lateral view of the sphincter mapping and treatment apparatus illustrating the mechanism used in one embodiment of an apparatus, useful with the method of the present invention, to increase the camber of the basket assembly.
Figure 9B:
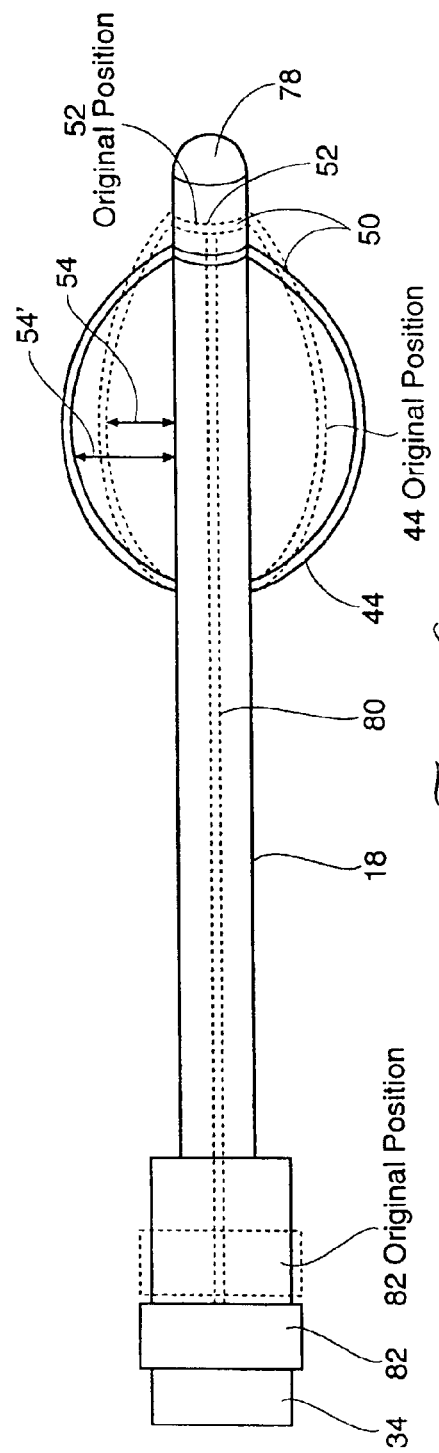
FIG. 9B is a similar view to 9A showing the basket assembly in an increased state of camber.
Figure 10:
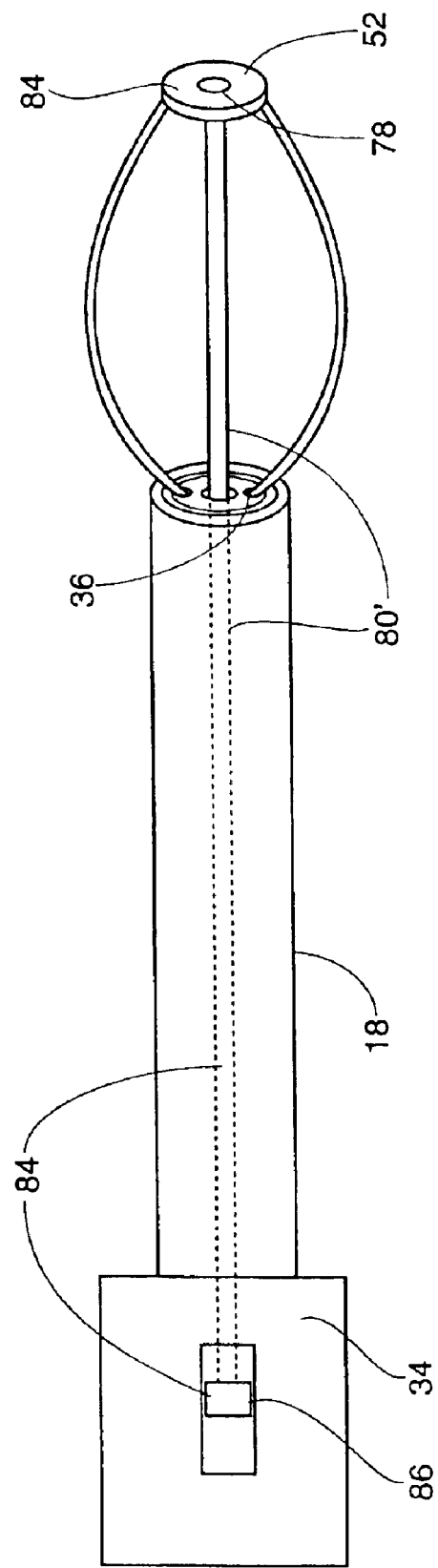
FIG. 10 is a lateral view of the sphincter mapping and treatment apparatus, useful with the method of the present invention, illustrating the deflection mechanism.

In one embodiment shown in FIGS. 9A and 9B, arms 44 are attached to distal basket cap 52 that in turn, moves freely over shaft 18, but is stopped distally by shaft cap 78. One or more pull wires 80 are attached to distal basket cap 52 and also to a movable fitting 82 in proximal fitting 34 of sphincter mapping and treatment apparatus 10. When pull wire 80 is pulled back by movable fitting 82, the camber 54 of basket assembly 50 increases to 54', increasing the force and the amount of contact applied by basket assembly 50 to sphincter wall 26 or an adjoining structure. Basket assembly 50 can also be deflected from side to side using deflection mechanism 84. This allows the physician to remotely point and steer the basket assembly within the body. In one embodiment shown in FIG. 10, deflection mechanism 84 includes a second pull wire 80' attached to shaft cap 78 and also to a movable slide 86 integral to proximal fitting 34.

Turning now to a discussion of energy delivery, suitable power sources 56 and energy delivery devices 88 that can be employed in one or more embodiments of the invention include: (i) a radio-frequency (RF) source coupled to an RF electrode, (ii) a coherent source of light coupled to an optical fiber, (iii) an incoherent light source coupled to an optical fiber, (iv) a heated fluid coupled to a catheter with a closed channel configured to receive the heated fluid, (v) a heated fluid coupled to a catheter with an open channel configured to receive the heated fluid, (vi) a cooled fluid coupled to a catheter with a closed channel configured to receive the cooled fluid, (vii) a cooled fluid coupled to a catheter with an open channel configured to receive the cooled fluid, (viii) a cryogenic fluid, (ix) a resistive heating source, (x) a microwave source providing energy from 915 MHz to 2.45 GHz and coupled to a microwave antenna, (xi) an ultrasound power source coupled to an ultrasound emitter, wherein the ultrasound power source produces energy in the range of 300 KHZ to 3 GHz, or (xii) a microwave source. For ease of discussion for the remainder of this application, the power source utilized is an RF source and electrode 88 is one or more RF electrodes 88. However, all of the other herein mentioned power sources and mapping electrodes are equally applicable to sphincter mapping and treatment apparatus 10.

When the power source is an RF energy source, power source 56, which will now be referred to as RF power source 56, supplies radio frequency energy, e.g., having a frequency in the range of about 400 kHz to about 10 mHz. Power source 56 may have multiple channels, delivering separately modulated power to each electrode 88. This reduces preferential heating that occurs when more energy is delivered to a zone of greater conductivity and less heating that occurs around RF electrodes 88 which are placed into less conductive tissue. If the level of tissue hydration or the blood infusion rate in the tissue is uniform, a single channel RF power source 56 may be used to provide power for generation of lesions 14 relatively uniform in size.

For embodiments using RF energy, RF electrode 88 may operated in either bipolar or a monopolar mode with a ground pad electrode. In a monopolar mode of delivering RF energy, a single electrode 88 is used in combination with an indifferent electrode patch 89 (or ground pad electrode) that is applied to the body to form the other electrical contact and complete an electrical circuit. Bipolar operation is possible when two or more RF electrodes 88 are used. Multiple RF electrodes 88 may be used. These electrodes may be cooled as described herein. RF electrodes 88 can be attached to electrode delivery member 60 by the use of soldering methods which are well known to those skilled in the art. Suitable solders include Megabond Solder supplied by the Megatrode Corporation (Milwaukee, Wis.).

Figure 11A:
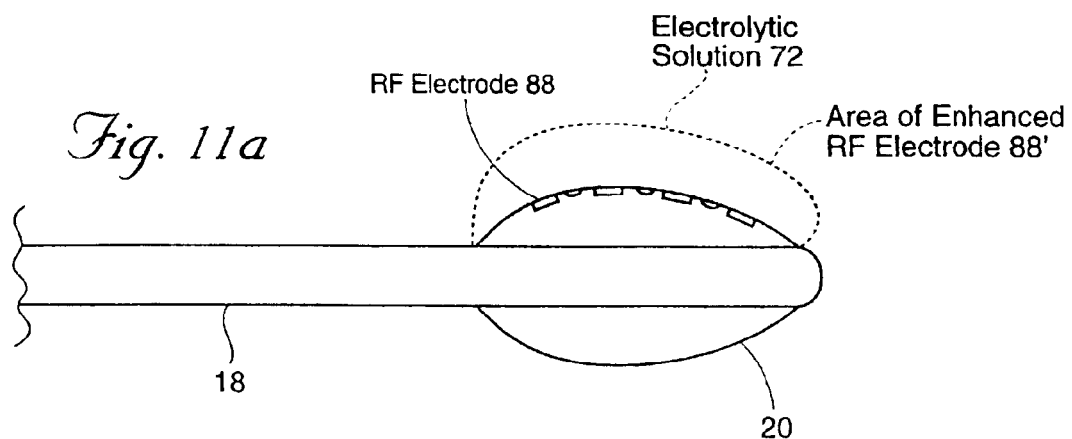
FIG. 11A is a lateral view illustrating the use of electrolytic solution to create an enhanced RF electrode.

Suitable electrolytic solutions 72 include saline, solutions of calcium salts, potassium salts, and the like. Electrolytic solutions 72 enhance the electrical conductivity of the targeted tissue at the treatment site 12. When a highly conductive fluid such as electrolytic solution 72 is infused into tissue the electrical resistance of the infused tissue is reduced, in turn, increasing the electrical conductivity of the infused tissue. As a result, there will be little tendency for tissue surrounding electrode 88 to desiccate (a condition described herein that increases the electrical resistance of tissue) resulting in a large increase in the capacity of the tissue to carry RF energy. Referring to FIG. 11A, a zone of tissue which has been heavily infused with a concentrated electrolytic solution 72 can become so conductive as to actually act as an enhanced electrode 88'. The effect of enhanced electrode 88' is to increase the amount of current that can be conducted to the treatment site 12, making it possible to heat a much greater volume of tissue in a given time period.

Figure 11B:
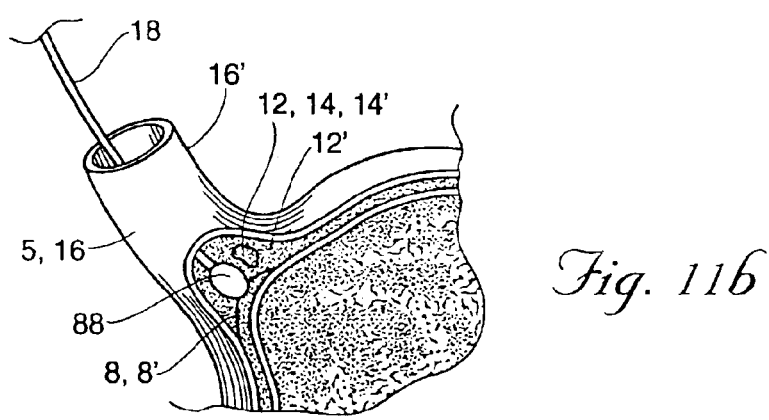
FIGS. 11B–11C are lateral views illustrating the use of nerves to conduct RF energy to a desired tissue site.
Figure 11C:
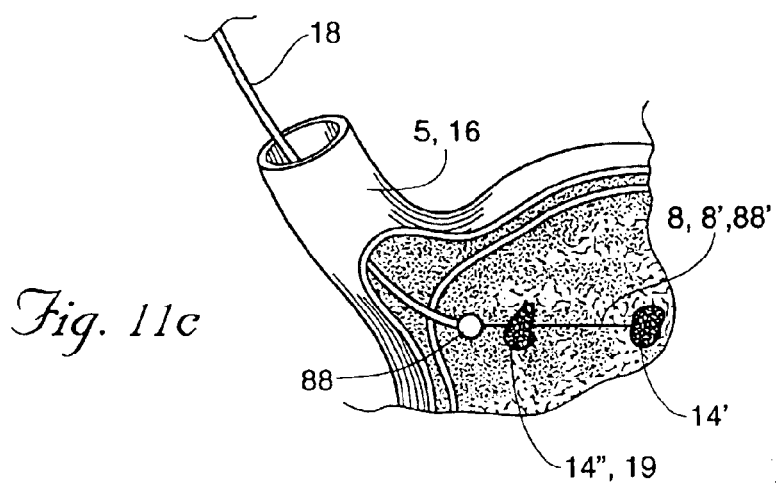

Referring now to FIGS. 11B and 11C, in other embodiments selected nerve fibers 8 can be used as an electrode or conduction path to conduct RF energy to a desired treatment site 12. In these and related embodiments, RF electrode 88 is positioned on or adjacent a nerve fiber 8 (preferably an afferent fiber 8') so as to electrically couple the RF electrode to the nerve fiber. RF energy is then conducted along nerve 8 to create a lesion 14 at some selected distance from the RF electrode 88 and or sphincter mucosal surface 16' of sphincter 16. Preferably this distance is 1 to 5 mm beneath the surface 16'. Parameters that can be used to control the distance of the lesion include one or more of the following: use of cooling a fluid (e.g. flow rate, temperature etc.), the RF power (e.g. wattage) level delivered to the electrode, duration of power delivery and total energy delivered (e.g. joules), nerve type, and nerve thickness. The use of nerves 8 to conduct RF energy presents the distinct advantage of being able to precisely control the delivery of energy to a desired treatment site to produce one or more lesions 14 via ohmic heating, while minimizing heating and injury to nearby non selected tissue 12'. In one embodiment shown in FIG. 11C, energy is delivered along nerve fiber 8' to produce a first or distal lesion 14' at distal position relative to the RF electrode 88. More proximal tissue can be protected via the use of a cooling solution 70 described herein. Continued delivery of RF energy and/or the attenuation of cooling, then results in the development of an expanded or second lesion 14" (which can be continuous or contiguous with the first lesion 14') starting at the more distal portions of the nerve adjacent the distal lesion 14' with subsequent travel of the lesion in a proximal direction along the nerve 8 to the more proximal portions near or adjacent electrode 88. In this way, one or more nerve fibers 8 can be used as an energy conduit and/or extended energy delivery device 88" to create multiple lesions in sphincter 16 including lesions both in submucosal muscle and nerve tissue in a single treatment session without having to reposition the energy delivery device. The creation of such multiple and/or continuous nerve and muscle lesions 14', 14" presents the further advantage of both tightening the sphincter 16 and creating areas of electrical block to minimize and/or eliminate TLSERS in a single delivery of energy and/or treatment session.

In various embodiments, RF electrodes 88 can have a variety of shapes and sizes. Possible shapes include, but are not limited to, circular, rectangular, conical and pyramidal. Electrode surfaces can be smooth or textured and concave or convex. The conductive surface area of electrode 88 can range from 0.1 mm2 to 100 cm2. It will be appreciated that other geometries and surface areas may be equally suitable. Other possible geometries include curved (forward or retrograde), spiral and oval.

Figure 12:
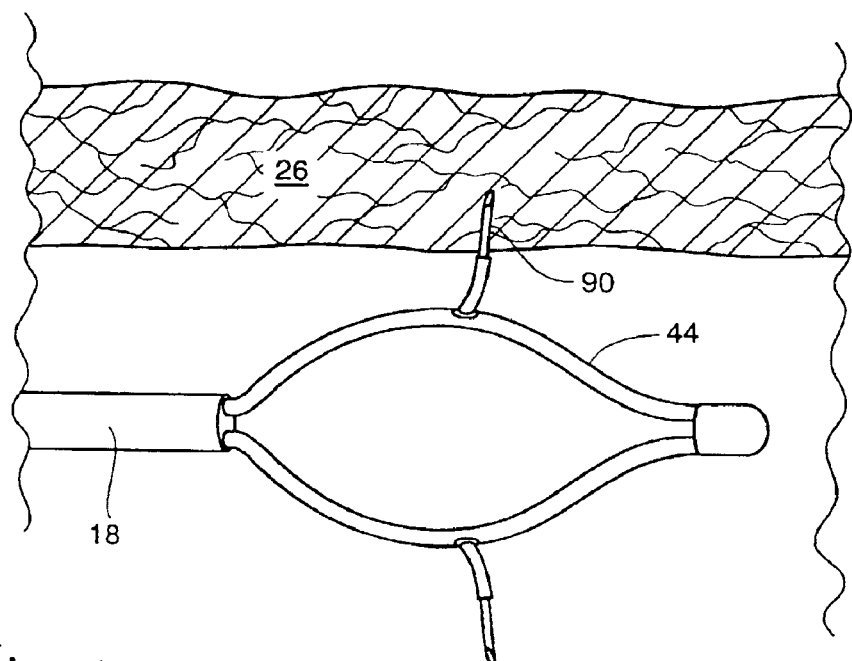
FIG. 12 is a lateral view of the basket assembly illustrating the use of needle electrodes.
Figure 13:
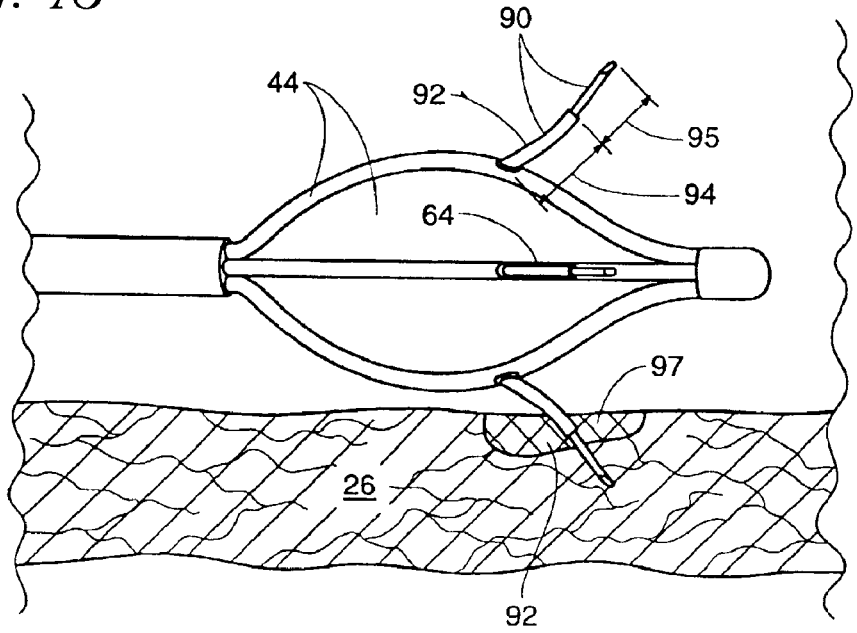
FIG. 13 is a lateral view illustrating the use of an insulation segment on the needle electrode to protect an area of tissue from RF energy.

In one embodiment, RF electrodes 88 can be in the shape of needles and of sufficient sharpness and length to penetrate into the smooth muscle of the esophageal wall, sphincter 16 or other anatomical structure. In this embodiment shown in FIGS. 12 and 13, needle electrodes 90 are attached to arms 44 and have an insulating layer 92, covering an insulated segment 94 except for an exposed segment 95. For purposes of this disclosure, an insulator or insulation layer is a barrier to either thermal, RF or electrical energy flow. Insulated segment 94 is of sufficient length to extend into sphincter wall 26 and minimize the transmission of RF energy to a protected site 97 near or adjacent to insulated segment 94 (see FIG. 13.). Typical lengths for insulated segment 94 include, but are not limited to, 1–4 mm. Suitable materials for needle electrodes 90 include, but are not limited to, 304 stainless steel and other stainless steels known to those skilled in the art. Suitable materials for insulating layer 92 include, but are not limited to, polyimides and polyamides.

Figure 14A:
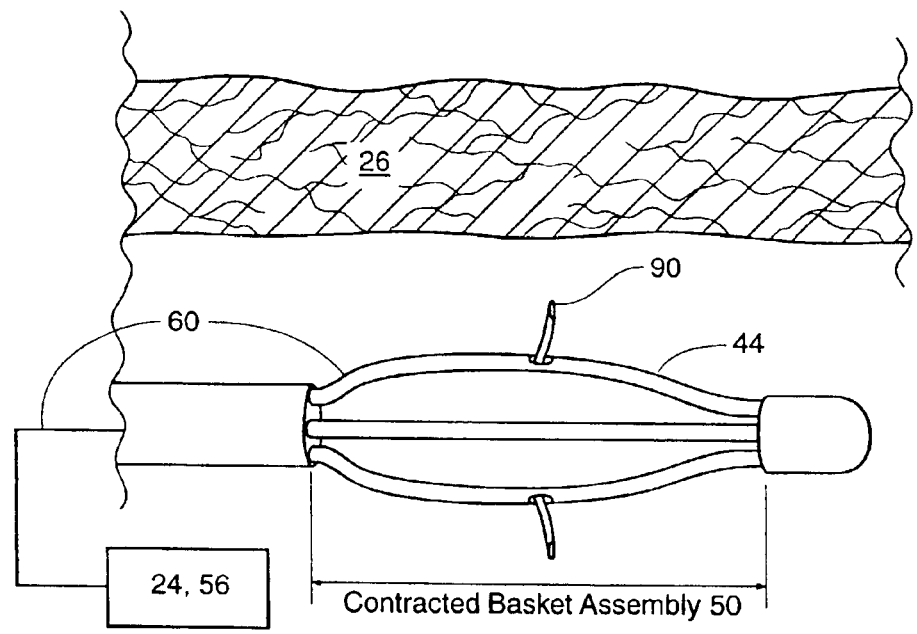
FIGS. 14A and 14B are lateral views illustrating the placement of needle electrodes into the sphincter wall by expansion of the basket assembly.
Figure 14B:
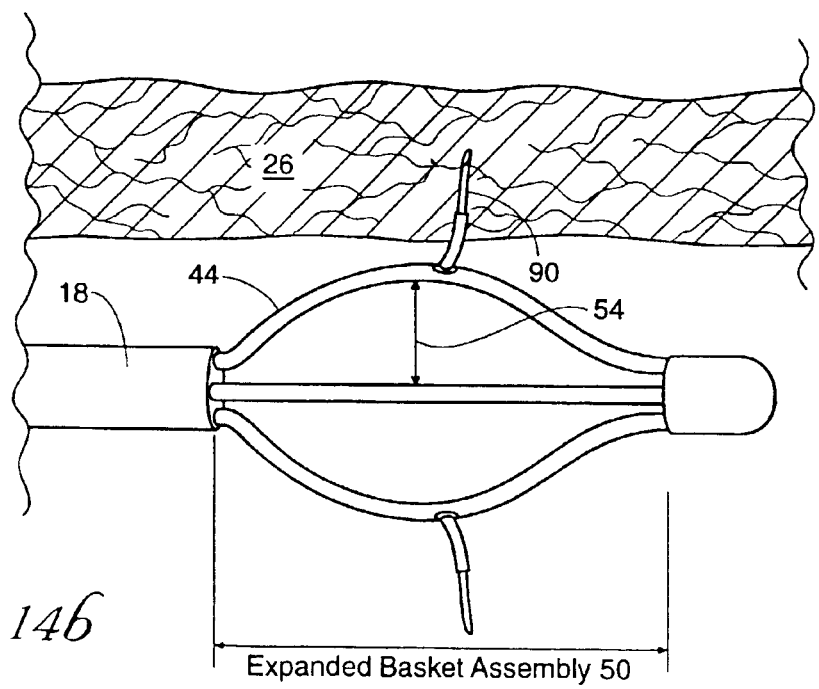

During introduction of sphincter mapping and treatment apparatus 10, basket assembly 50 is in a contracted state. Once sphincter mapping and treatment apparatus 10 is properly positioned at the treatment site 12, needle electrodes 90 are deployed by expansion of basket assembly 50, resulting in the protrusion of needle electrodes 90 into the smooth muscle tissue of sphincter wall 26 (refer to FIGS. 14A and 14B). The depth of needle penetration is selectable from a range of 0.5 to 5 mm and is accomplished by indexing movable fitting 82 so as to change the camber 54 of arm 44 in fixed increments that can be selectable in a range from 0.1 to 4 mms. Needle electrodes 90 are coupled to power source 56 via insulated wire 60.

Figure 15:
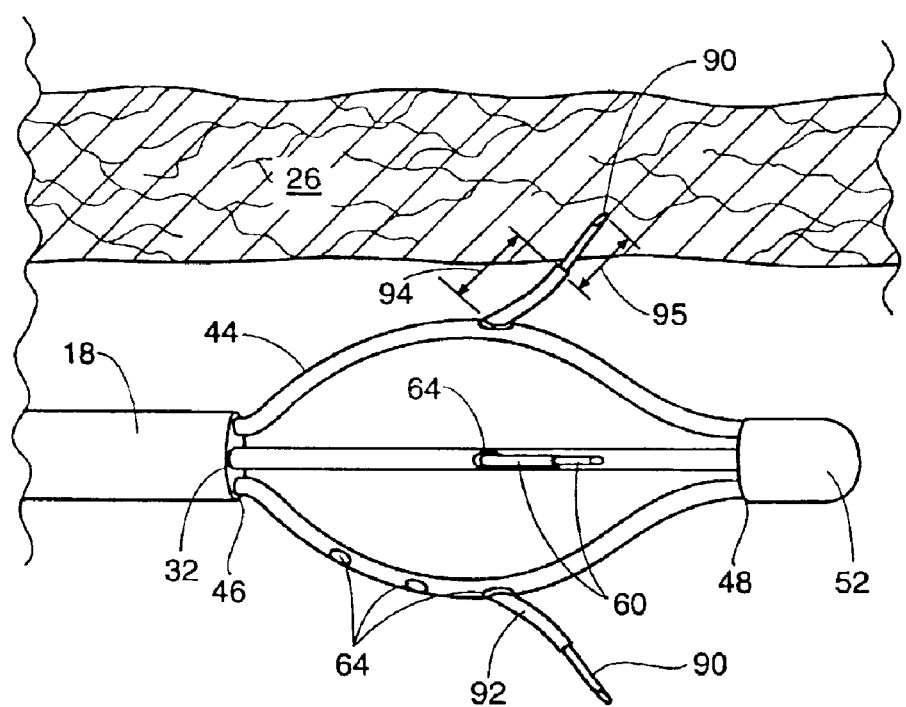
FIG. 15 is a lateral view illustrating placement of needle electrodes into the sphincter wall by advancement of an electrode delivery member out of apertures in the basket arms.
Figure 16:
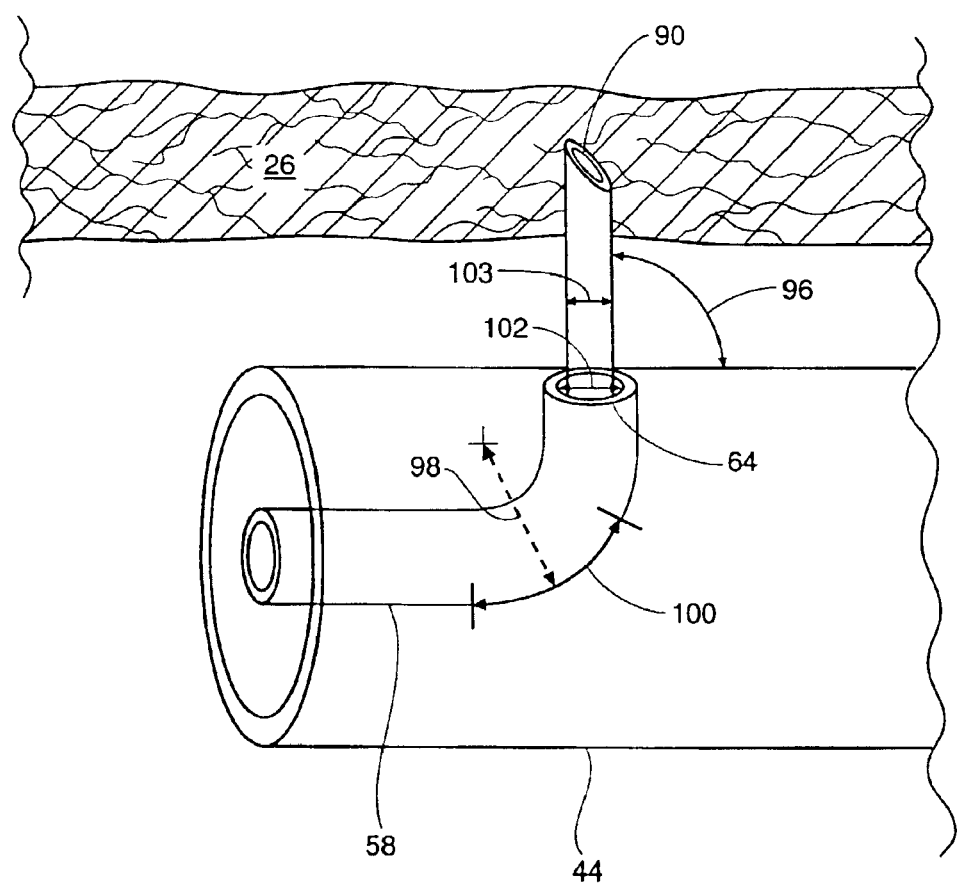
FIG. 16 is a cross sectional view illustrating the configuration of a basket arm aperture used to select and maintain a penetration angle of the needle electrode into the sphincter wall.

In another embodiment of sphincter mapping and treatment apparatus 10 shown in FIG. 15, needle electrodes 90 are advanced out of apertures 64 in basket arms 44 into the smooth muscle of the esophageal wall or other sphincter 16. In this case, needle electrodes 90 are electrically coupled to RF power source 56 by electrode delivery member 60. In this embodiment, the depth of needle penetration is selectable via means of tapered sections 66 or stepped sections 68 located in apertures 64. Referring now to FIG. 16, apertures 64 and needle electrodes 90 are configured such that the penetration angle 96 (also called an emergence angle 96) of needle electrode 90 into sphincter wall 26 remains sufficiently constant during the time needle electrode 90 is being inserted into sphincter wall 26, such that there is no tearing or unnecessary trauma to sphincter wall tissue. This is facilitated by the selection of the following parameters and criteria: i) the emergence angle 96 of apertures 64 which can vary from 1 to 90°, ii) the arc radius 98 of the curved section 100 of aperture 64 which can vary from 0.001 to 2 inch, iii) the amount of clearance between the aperture inner diameter 102 and the needle electrode outside diameter 103 which can very between 0.001" and 0.1"; and, iv) use of a lubricous coating on electrode delivery member 60 such as a Teflon® or other coatings well known to those skilled in the art including liquid silicone coatings. Also in this embodiment, insulated segment 94 can be in the form of a sleeve that may be adjustably positioned at the exterior of needle electrode 90.

Figure 17:
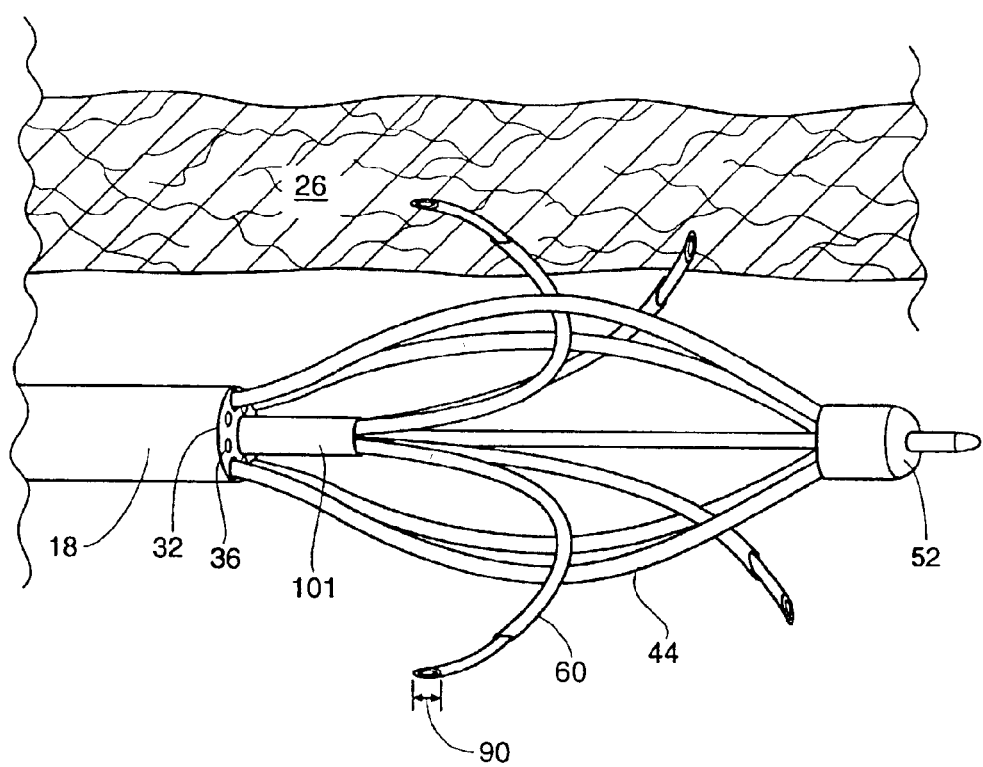
FIG. 17 is a lateral view illustrating placement of needle electrodes into the sphincter wall by advancement of an electrode delivery member directly out of the distal end of the shaft.
Figure 18A:
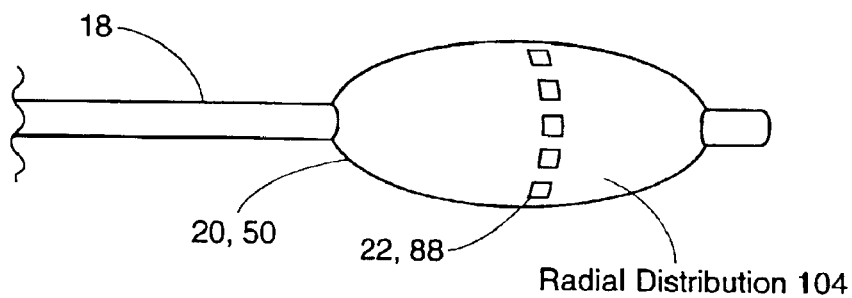
FIG. 18A is a lateral view illustrating a radial distribution of electrodes on the expandable mapping assembly of an apparatus useful with the method of the present invention.
Figure 18B:
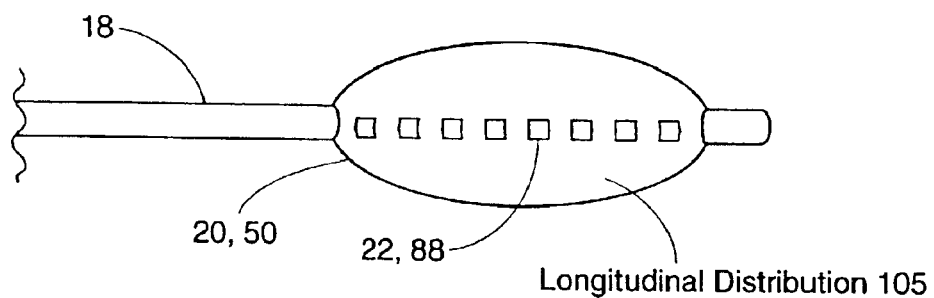
FIG. 18B is a lateral view illustrating a longitudinal distribution of electrodes on the expandable mapping assembly useful with the method of the present invention.
Figure 18C:
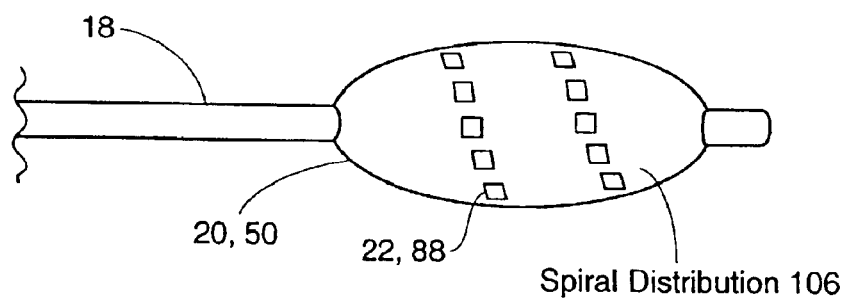
FIG. 18C is a lateral view illustrating a spiral distribution of electrodes on the expandable mapping assembly useful with the method of the present invention.
Figure 18D:
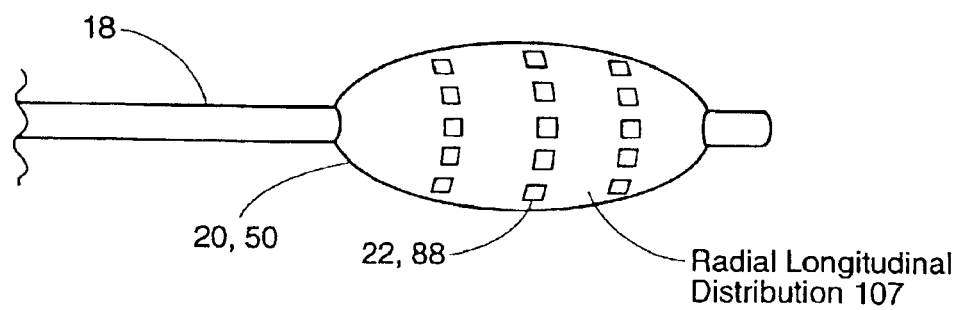
FIG. 18D is a lateral view illustrating a radial-longitudinal distribution of electrodes on the expandable mapping assembly useful with the method of the present invention.

In another alternative embodiment shown in FIG. 17, electrode delivery member 60 with attached needle electrodes 90, can exit from shaft lumen 36 at distal shaft end 32 and be positioned into contact with sphincter wall 26. This process may be facilitated by use of a hollow guiding member 101, known to those skilled in the art as a guiding catheter, through which electrode delivery member 60 is advanced. Guiding catheter 101 may also include tapered sections 66 or stepped sections 68 at its distal end to control the depth of penetration of needle electrode 90 into sphincter wall 26.

RF energy flowing through tissue causes heating of the tissue due to absorption of the RF energy by the tissue and ohmic heating due to electrical resistance of the tissue. This heating can cause injury to the affected cells and can be substantial enough to cause cell death, a phenomenon also known as cell necrosis. For ease of discussion for the remainder of this application, cell injury will include all cellular effects resulting from the delivery of energy from electrode 88 up to, and including, cell necrosis. Cell injury can be accomplished as a relatively simple medical procedure with local anesthesia. In one embodiment, cell injury proceeds to a depth of approximately 1–4 mm from the surface of the mucosal layer of sphincter 16 or that of an adjoining anatomical structure.

Referring now to FIGS. 18A, 18B, 18C and 18D, mapping electrodes 22, RF electrodes 88 and/or apertures 64 may be distributed in a variety of patterns along expandable mapping assembly 20 or basket assembly 50 to facilitate mapping and in order to produce a desired placement and pattern of lesions 14. Typical electrode (both mapping and RF varieties) and aperture distribution patterns include, but are not limited to, a radial distribution 104 (refer to FIG. 18A), a longitudinal distribution 105 (refer to FIG. 18B), a spiral distribution 106 (refer to FIG. 18C) and a combination of longitudinal and radial distributions 107 (refer to FIG. 18D). It will be appreciated that other combinations, patterns and geometries for electrode and aperture placement, may also be suitable. These electrodes may be cooled as described hereafter.

Figure 19:
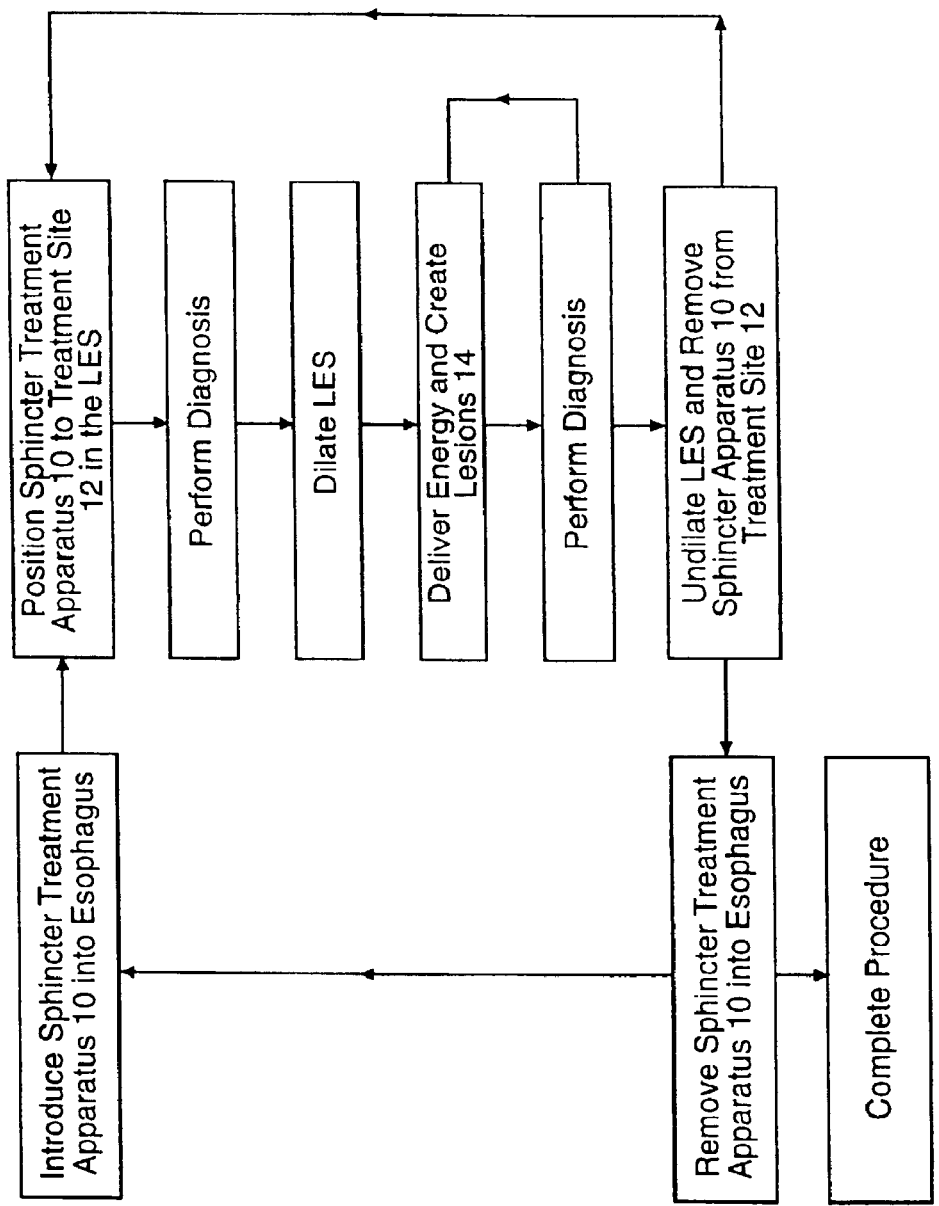
FIG. 19 is a flow chart illustrating the sphincter treatment method of the current invention.

FIG. 19 is a flow chart illustrating one embodiment of the procedure for using sphincter mapping and treatment apparatus 10. In this embodiment, sphincter mapping and treatment apparatus 10 is first introduced into the esophagus under local anesthesia. Sphincter mapping and treatment apparatus 10 can be introduced into the esophagus by itself or through a lumen in an endoscope (not shown), such as disclosed in U.S. Pat. Nos. 5,448,990 and 5,275,608, incorporated herein by reference, or similar esophageal access devices known to those skilled in the art. Basket assembly 50 is expanded as described herein. This serves to temporarily dilate the LES or sufficiently to efface a portion of or all of the folds of the LES. In an alternative embodiment, esophageal dilation and subsequent LES fold effacement can be accomplished by insufflation of the esophagus (a known technique) using gas introduced into the esophagus through shaft lumen 36, or an endoscope or similar esophageal access device as described above. Once treatment is completed, basket assembly 50 is returned to its predeployed or contracted state and sphincter mapping and treatment apparatus 10 is withdrawn from the esophagus. This results in the LES returning to approximately its pretreatment state and diameter. It will be appreciated that the above procedure is applicable in whole or part to the treatment of other sphincters in the body.

Figure 20:
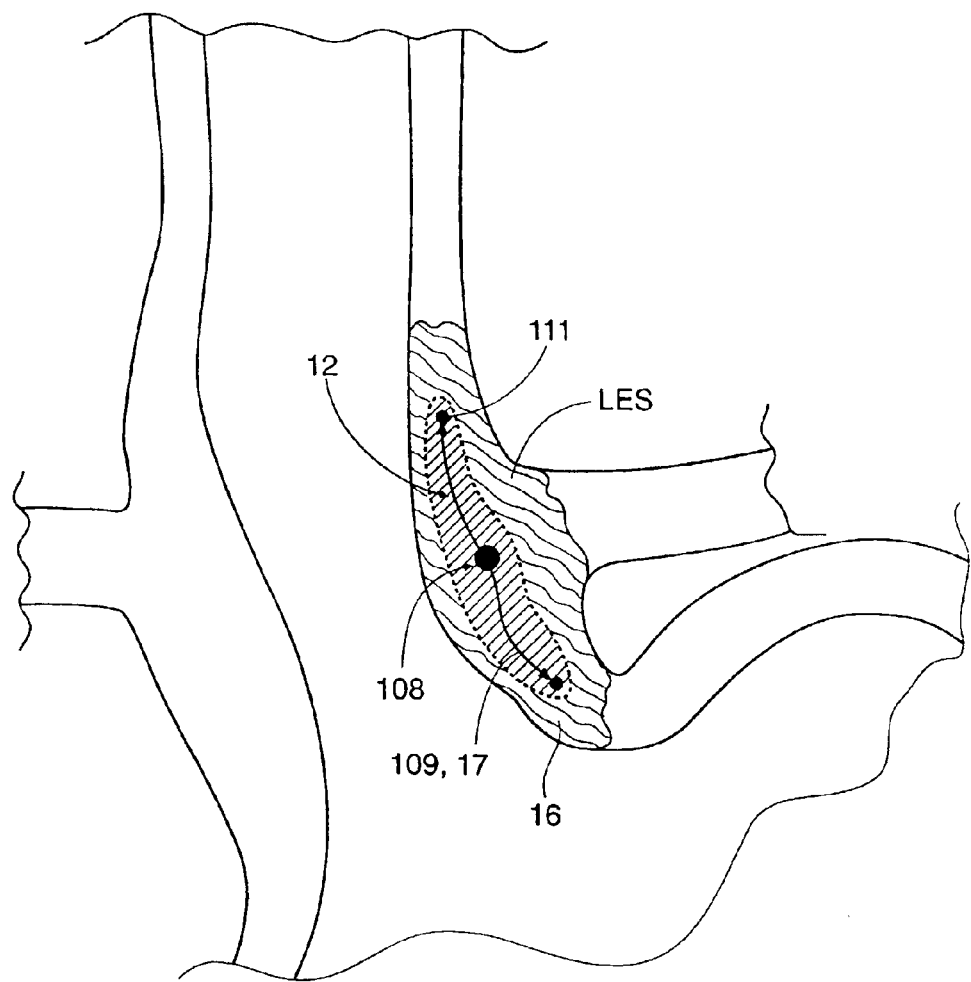
FIG. 20 is a lateral view of sphincter smooth muscle tissue illustrating electromagnetic foci and pathways for the origination and conduction of aberrant electrical signals in the smooth muscle of the lower esophageal sphincter or other tissue.

As discussed previously, controller 24 and electropotential map 27 are used by the physician to diagnose abnormalities and pathologies within sphincter 16 and adjoining structures. More specifically, they are used to identify gastric electrical signals 17 and electrical events that include depolarization, contraction and repolarization. Referring now to FIG. 20, this information is used by the physician to determine target treatment sites 12 in the LES or adjoining anatomical structures that are acting as electrical foci 108 or electrically conductive pathways 109 for aberrant electrical signals 111 causing abnormal or otherwise inappropriate relaxation of the smooth muscle of the LES or other sphincter 16. These targeted treatment sites 12 are then treated as described herein so as to create lesions 14 which disrupt, block or otherwise prevent the generation and transmission of sufficient aberrant electrical signals 111 to cause relaxation of the LES or other sphincter wall 26.

A variety of other diagnostic methods can be employed as an adjunct to surface mapping of sphincter wall 26. These method include, but are not limited to, the following: (i) visualization of the interior surface of the esophagus via an endoscope or other viewing apparatus inserted into the esophagus, (ii) visualization of the interior morphology of the esophageal wall using ultrasonography to establish a baseline for the tissue to be treated; and, (iii) impedance measurement to determine the electrical conductivity between the esophageal mucosal layers and sphincter mapping and treatment apparatus 10.

In one embodiment of the invention, impedance measurement is used as a tool to locate the position of the nerve during either the diagnostic or treatment phases of the procedure. In these and related embodiments, the physician uses an impedance sensor 140 (described herein) positioned on one of electrodes 22, 88 and 90 or mapping assembly 20 to locate the position of the nerve 8 to be ablated, and/or used as a conductive pathway for the delivery of energy to a selected gastric treatment site 12. Specifically, nerve 8, 8' is located by a decrease in measured tissue impedance relative to a non-nerve portion of tissue. During or after the delivery of energy to nerve 8, 8' the ablation of the selected nerve can be monitored, quantified or titrated through the use of tissue impedance measurement.

In related embodiments, a similar technique can be used to locate a vagus nerve 8" or other nerve 8, 8', 8" that is desired to be protected during the treatment phase of the procedure. Further, during the delivery of energy to the treatment site 12, sensor 140 the can be positioned at or adjacent the nerve to be protected to monitor nerve impedance levels during the treatment of energy. Sensor 140 is coupled to a control system described here in. If the impedance level at or near nerve 8 exceeds a predetermined value, the delivery of energy to electrode 88 or 90 is shut off or decreased by the control system for the position.

In the treatment phase of the procedure, the delivery of energy to treatment site 12 can be conducted under feedback control, manually or by a combination of both. Feedback control (described herein) enables sphincter mapping and treatment apparatus 10 to be positioned and retained in the esophagus during treatment with minimal attention by the physician. RF electrodes 88 can be multiplexed in order to treat the entire targeted treatment site 12 or only a portion thereof. Feedback can be included and is achieved by the use of one or more of the following methods: (i) visualization, (ii) impedance measurement, (iii) ultrasonography, (iv) temperature measurement; and, (v) sphincter contractile force measurement via manometry. The feedback mechanism permits the selected on-off switching of different RF electrodes 88 in a desired pattern, which can be sequential from one electrode 88 to an adjacent electrode 88, or can jump around between non-adjacent RF electrodes 88. Individual RF electrodes 88 are multiplexed and volumetrically controlled by controller 24.

Figure 21:
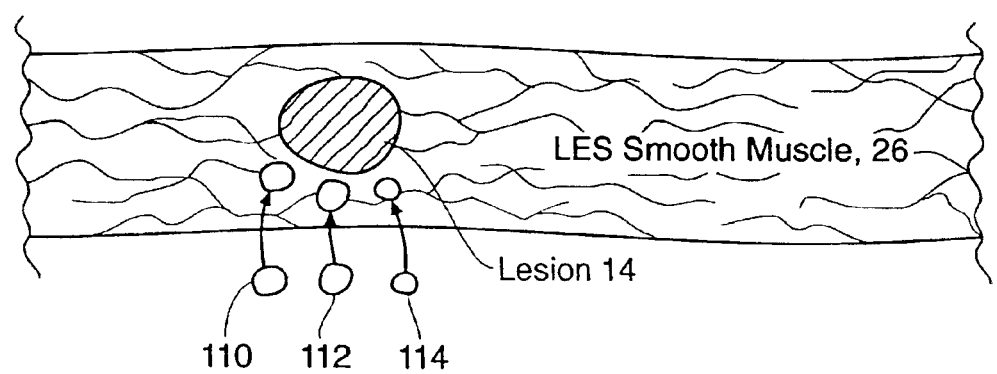
FIG. 21 is a lateral view of a sphincter wall illustrating the infiltration of tissue healing cells into a lesion in the smooth tissue of a sphincter following treatment with the sphincter treatment apparatus.
Figure 22:
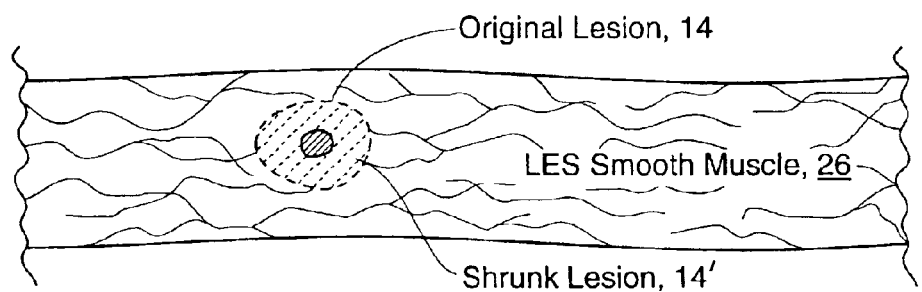
FIG. 22 is a view similar to that of FIG. 21 illustrating shrinkage of the lesion site caused by cell infiltration.
Figure 23:
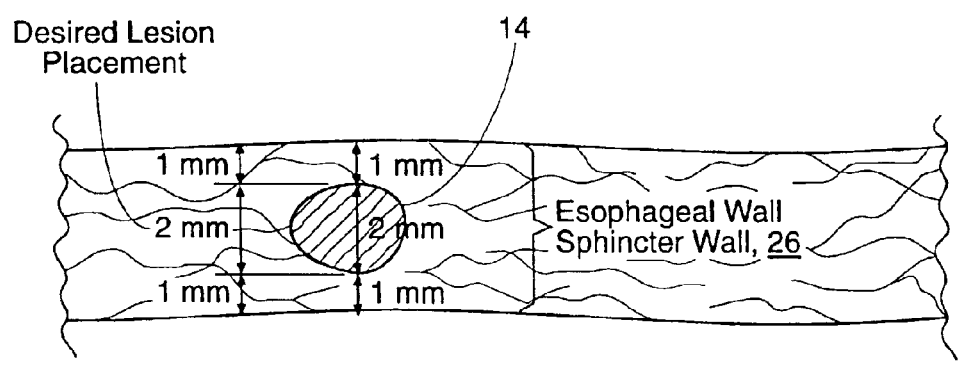
FIG. 23 is a lateral view of the esophageal wall illustrating the preferred placement of lesions in the smooth muscle layer of a esophageal sphincter.

The area and magnitude of cell injury in the LES or sphincter 16 can vary. However, it is desirable to deliver sufficient energy to the targeted treatment site 12 to be able to achieve tissue temperatures in the range of 55–95° C. and produce lesions 14 at depths ranging from 1–4 mm from the interior surface of the LES or sphincter wall 26. Typical energies delivered to the esophageal wall include, but are not limited to, a range between 100 and 50,000 joules per electrode 88. It is also desirable to deliver sufficient energy such that the resulting lesions 14 have a sufficient magnitude and area of cell injury to cause an infiltration of lesion 14 by fibroblasts 110, myofibroblasts 112, macrophages 114 and other cells involved in the tissue healing process (refer to FIG. 21). As shown in FIG. 22, these cells cause a contraction of tissue around lesion 14, decreasing its volume and, or altering the biomechanical properties at lesion 14 so as to result in a tightening of LES or sphincter 16. These changes are reflected in transformed lesion 14' shown in FIG. 19B. The diameter of lesions 14 can vary between 0.1 to 4 mm. It is preferable that lesions 14 are less than 4 mm in diameter in order to reduce the risk of thermal damage to the mucosal layer. In one embodiment, a 2 mm diameter lesion 14 centered in the wall of the smooth muscle provides a 1 mm buffer zone to prevent damage to the mucosa, submucosa and adventitia, while still allowing for cell infiltration and subsequent sphincter tightening on approximately 50% of the thickness of the wall of the smooth muscle (refer to FIG. 23).

Figure 24:
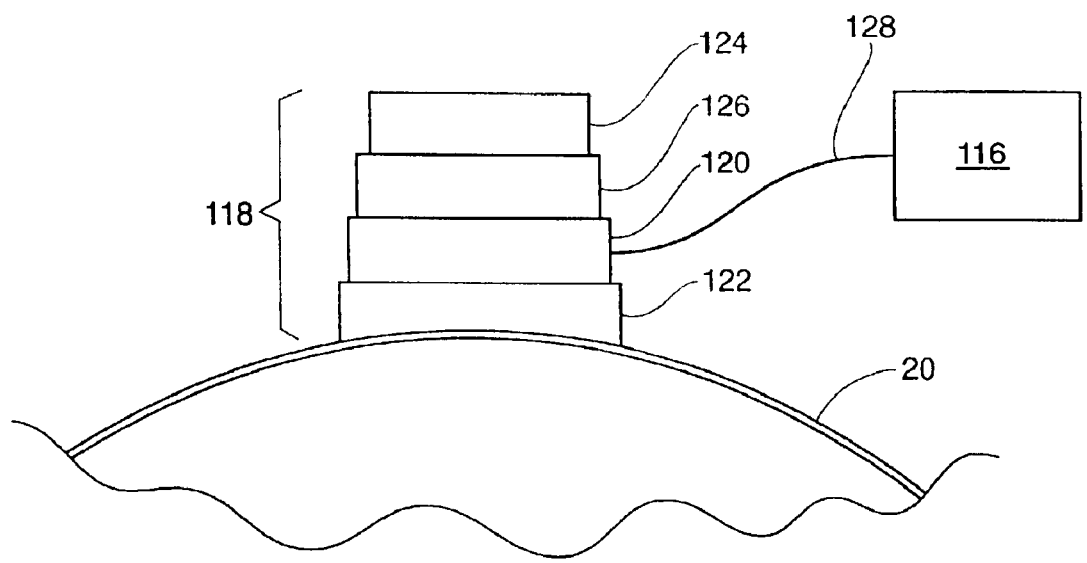
FIG. 24 is a lateral view illustrating an ultrasound transducer, ultrasound lens and power source of an embodiment useful with the method of the present invention.
Figure 25B:
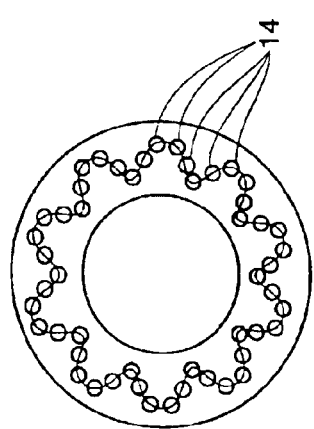
FIGS. 25A–D are lateral views of the sphincter wall illustrating various patterns of lesions created in an embodiment of the method of the present invention.
Figure 25D:
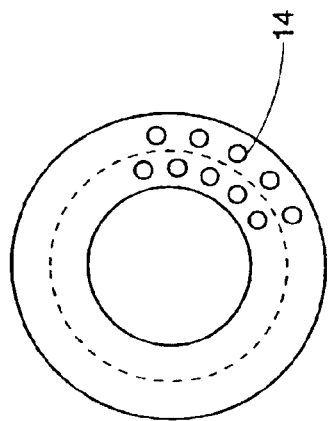
Figure 25A:
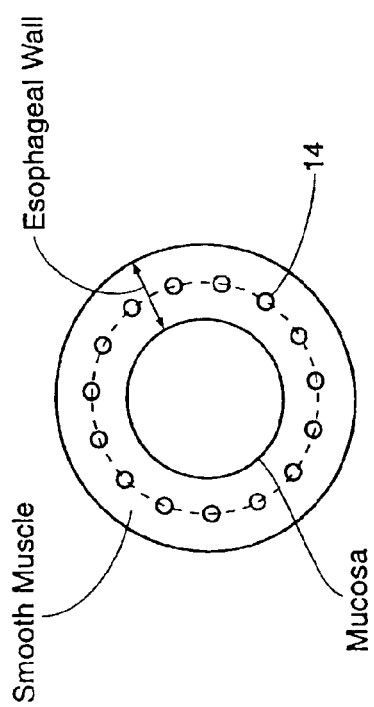
Figure 25C:
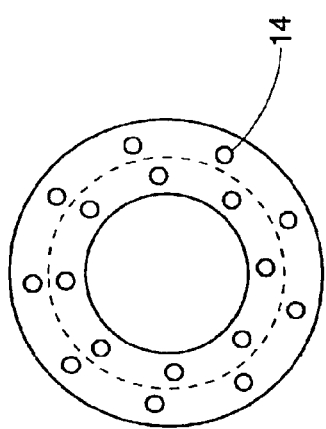

From a diagnostic standpoint, it is desirable to image the interior surface and wall of the LES or other sphincter 16, including the size and position of created lesions 14. It is desirable to create a map of these structures which can be inputted to controller 24 and used to direct the delivery of energy to treatment site 12. Referring to FIG. 24, this can be accomplished through the use of ultrasonography (a known procedure) which involves the use of an ultrasound power source 116 coupled to one or more ultrasound transducers 118 that are positioned on expandable mapping assembly 20 or basket assembly 50. An output is associated with ultrasound power source 116.

Each ultrasound transducer 118 can include a piezoelectric crystal 120 mounted on a backing material 122 that is in turn, attached to expandable mapping assembly 20 or basket assembly 50. An ultrasound lens 124, fabricated on an electrically insulating material 126, is mounted over piezoelectric crystal 120. Piezoelectric crystal 120 is connected by electrical leads 128 to ultrasound power source 116. Each ultrasound transducer 118 transmits ultrasound energy into adjacent tissue. Ultrasound transducers 118 can be in the form of an imaging probe such as Model 21362, manufactured and sold by Hewlett Packard Company, Palo Alto, Calif. In one embodiment, two ultrasound transducers 118 are positioned on opposite sides of expandable mapping assembly 20 or basket assembly 50 to create an image depicting the size and position of lesion 14 in selected sphincter 16.

It is desirable that lesions 14 are predominantly located in the smooth muscle layer of selected sphincter 16 at the depths ranging from 1 to 4 mm from the interior surface of sphincter wall 26. However, lesions 14 can vary both in number and position within sphincter wall 26. It may be desirable to produce a pattern of multiple lesions 14 within the sphincter smooth muscle tissue in order to obtain a selected degree of tightening of the LES or other sphincter 16. Typical lesion patterns shown in FIGS. 25A–D include, but are not limited to, (i) a concentric circle of lesions 14 all at fixed depth in the smooth muscle layer evenly spaced along the radial axis of sphincter 16, (ii) a wavy or folded circle of lesions 14 at varying depths in the smooth muscle layer evenly spaced along the radial axis of sphincter 16, (iii) lesions 14 randomly distributed at varying depths in the smooth muscle, but evenly spaced in a radial direction; and, (iv) an eccentric pattern of lesions 14 in one or more radial locations in the smooth muscle wall. Accordingly, the depth of RF and thermal energy penetration sphincter 16 is controlled and selectable. The selective application of energy to sphincter 16 may be the even penetration of RF energy to the entire targeted treatment site 12, a portion of it, or applying different amounts of RF energy to different sites depending on the condition of sphincter 16. If desired, the area of cell injury can be substantially the same for every treatment event.

In other embodiments shown in FIGS. 25E–G, lesions 14 are configured to produce an area of electrical block 19 (also called blockage area 19 or area 19) to a myoelectric or gastric signal 17, particularly a signal such as a gastric arrythimia 17' causing a TLSER. The area of electrical block is achieved by delivering sufficient energy to make the tissue comprising all or a portion of areas 19 nonconducting. This can be accomplished by heating the tissue sufficiently to denature proteins, destroy cell membrane, dehydrate/dessicate the tissue or otherwise altering its physically properties. Blockage area 19 can also be achieved by delivering sufficient energy to damage or destroy a nerve pathway within area 19 or a mechanical or chemo receptor 9, 9'.

In various embodiments, blockage area 19 can be placed by the physician in a number of locations including the cardia, fundus, angle of his, LES and esophagus. The placement of area 19 in the cardia can include positioning lesions 14 and blockage area 19 in or along a nerve pathway within the cardia or fundus. In still another related embodiment, area 19 comprises a lesion 14 placed within or along an afferent nerve 8' leading from a mechano or chemo receptor in the cardia or fundus to the another area of the cardia, or LES (see FIG. 25F). In one preferred embodiment area 19 is placed within the cardia and blocks gastric signals 17 from the fundus or cardia to the LES including signals 17 from a mechano receptor or chemo receptor in the cardia or fundus to the cardia or LES (see FIG. 25G). Shapes for area 19 include but are not limited to substantial linear, rectangular, circular, semicircular, annular, semi-annular and combinations thereof. In specific embodiments, area 19 can be comprise a linear or partially annular shaped positioned in the cardia (see FIG. 25G).

Figure 26:
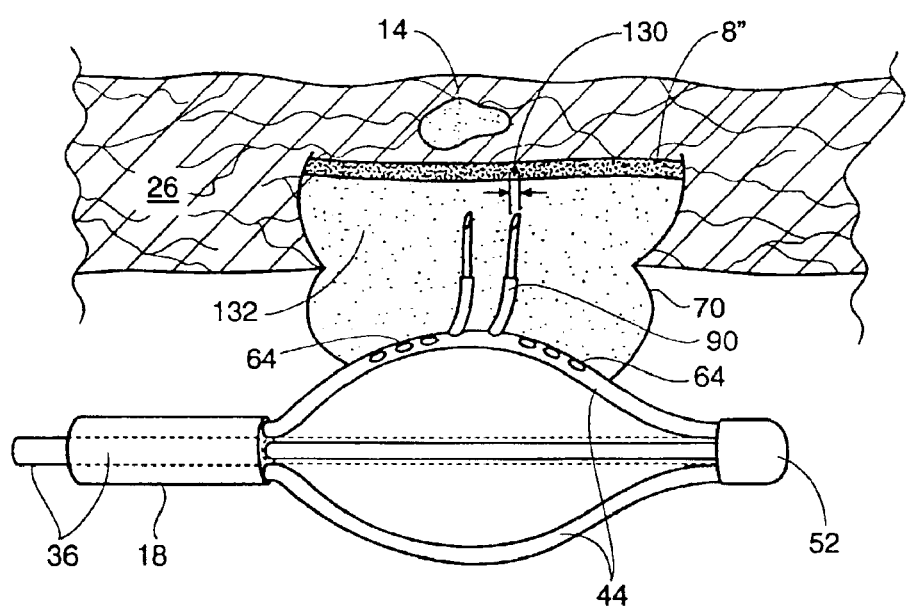
FIG. 26 is a lateral view of the sphincter wall illustrating the delivery of cooling fluid to the electrode-tissue interface and the creation of cooling zones.
Figure 27:
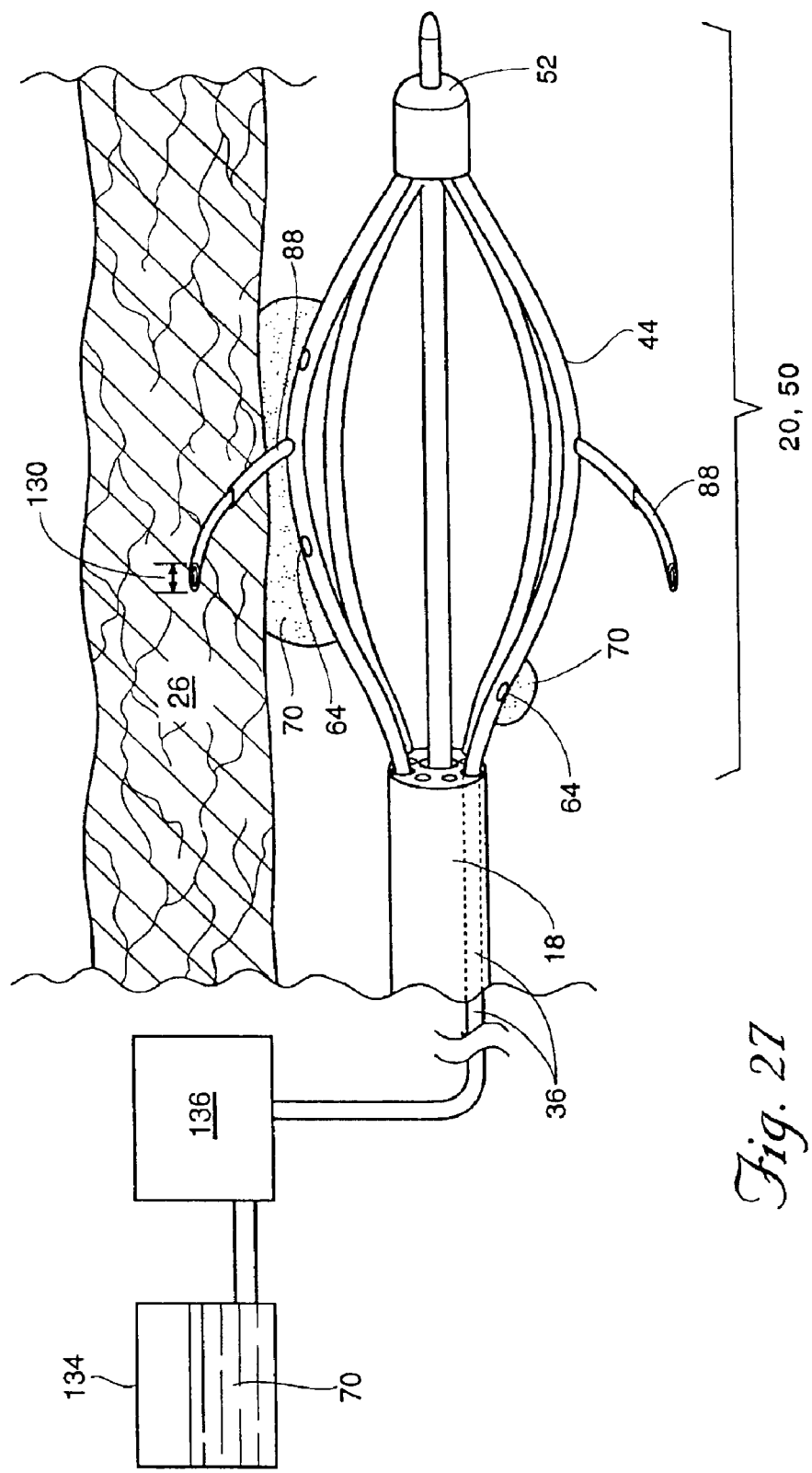
FIG. 27 depicts the flow path, fluid connections and control unit employed to deliver fluid to the electrode-tissue interface.

Referring to FIG. 26, it may be desirable to cool all or a portion of the area near the electrode-tissue interface 130 before, during or after the delivery of energy in order to reduce the degree and area of cell injury. Specifically, the use of cooling preserves the mucosal layers of sphincter wall 26 and protects, or otherwise reduces the degree of cell damage to cooled zone 132 in the vicinity of lesion 14. In one embodiment the use of cooling is used to protect and/or minimize damage to a vagus nerve or other nerve 8" associated with a swallowing reflex. Referring now to FIG. 27, this can be accomplished through the use of a cooling solution 70 that is delivered by apertures 64 which is in fluid communication with shaft lumen 36 that is, in turn, in fluid communication with fluid reservoir 134 and a control unit 136, whose operation is described herein, that controls the delivery of the fluid.

Figure 28:
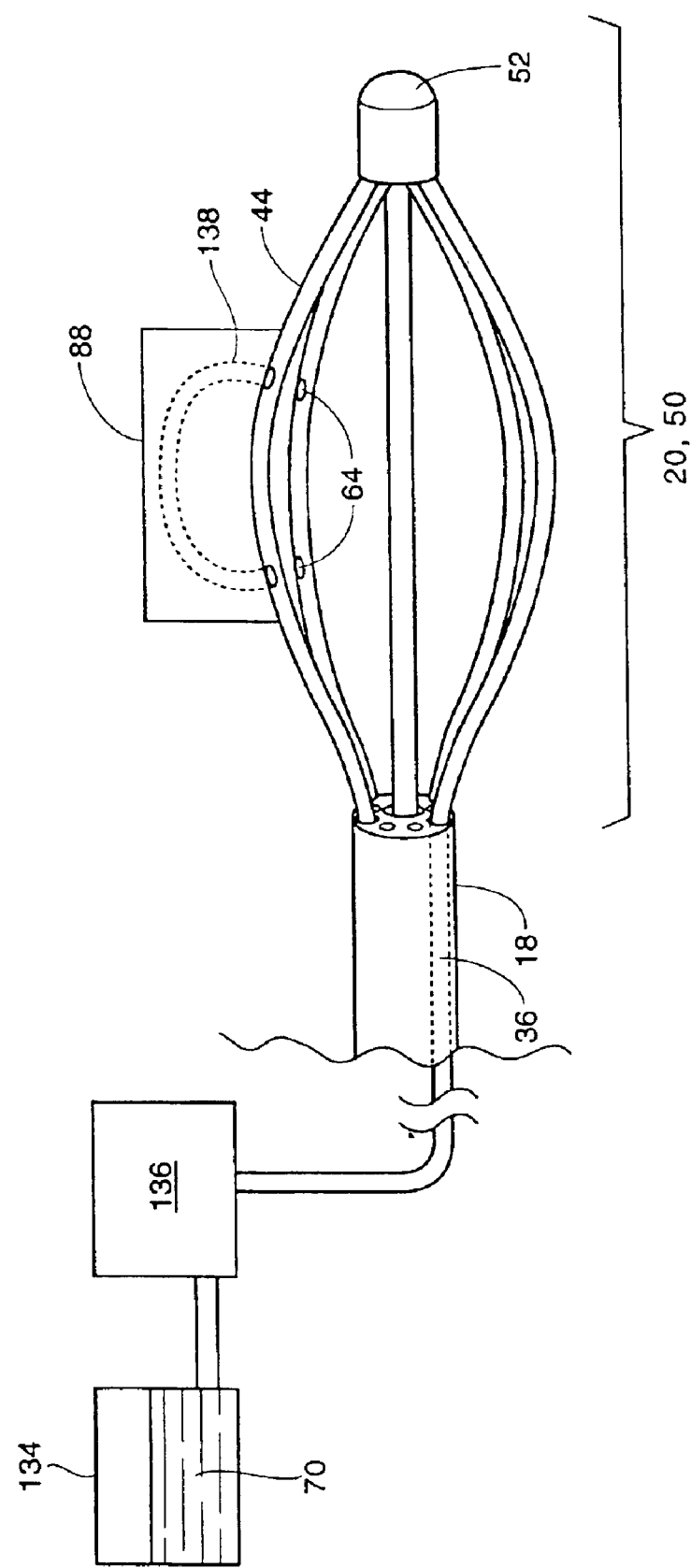
FIG. 28 depicts the flow path, fluid connections and control unit employed to deliver fluid to the RF electrodes.

Similarly, it may also be desirable to cool all or a portion of the electrode 88. The rapid delivery of heat through electrode 88, may result in the build up of charred biological matter on electrode 88 (from contact with tissue and fluids e.g., blood) that impedes the flow of both thermal and electrical energy from electrode 88 to adjacent tissue and causes an electrical impedance rise beyond a cutoff value set on RF power source 56. A similar situation may result from the desiccation of tissue adjacent to electrode 88. Cooling of the electrode 88 can be accomplished by cooling solution 70 that is delivered by apertures 64 as described previously. Referring now to FIG. 28, electrode 88 may also be cooled via a fluid channel 138 in electrode 88 that is in fluid communication with fluid reservoir 134 and control unit 136.

Figure 29:
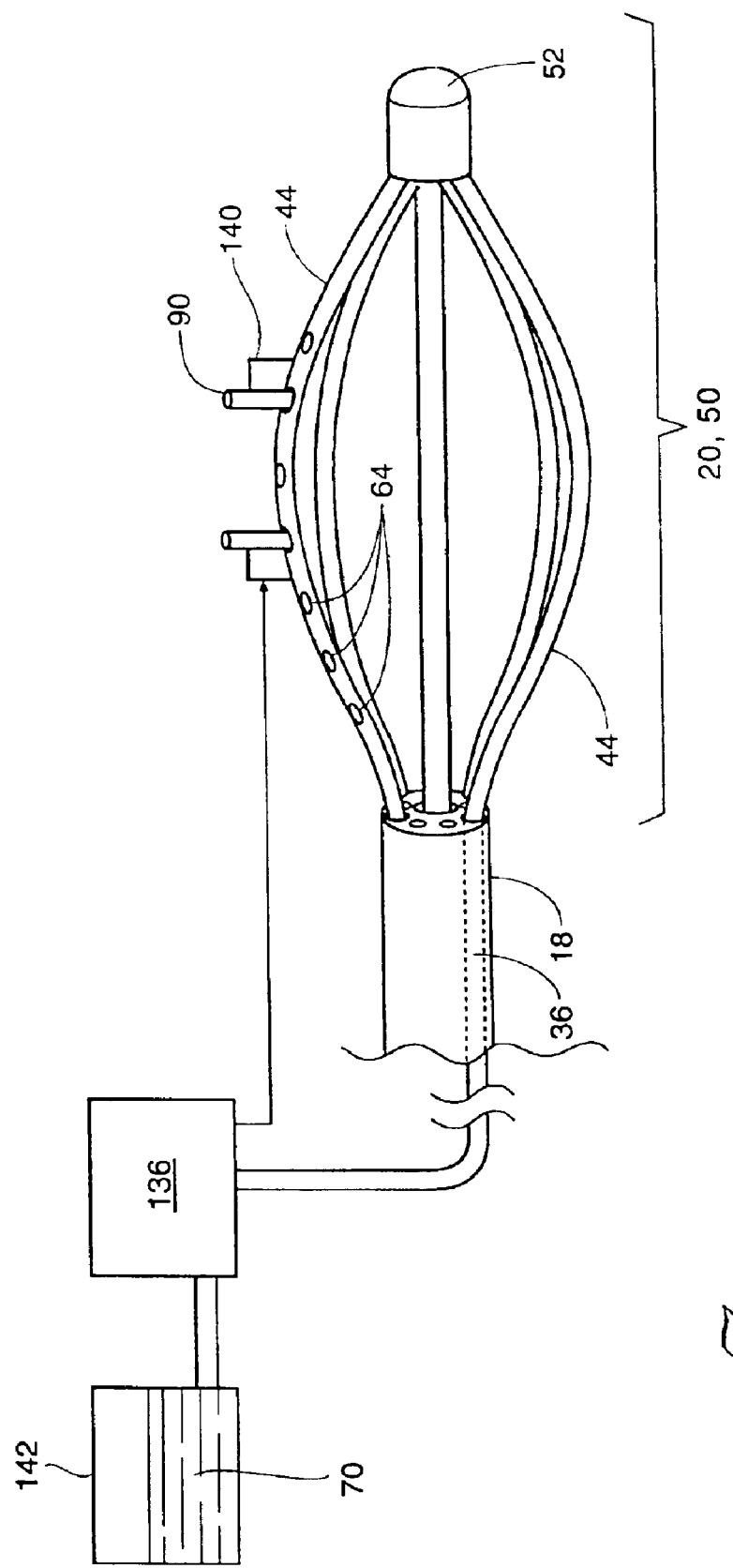
FIG. 29 is an enlarged lateral view illustrating the placement of sensors on the expansion device or basket assembly.

As shown in FIG. 29, one or more sensors 140 may be positioned adjacent to or on electrode 88 for sensing the temperature of sphincter tissue at treatment site 12. More specifically, sensors 140 permit accurate determination of the surface temperature of sphincter wall 26 at electrode-tissue interface 130. This information can be used to regulate both the delivery of energy and cooling solution 70 to the interior surface of sphincter wall 26. In various embodiments, sensors 140 can be positioned at any position on expandable mapping assembly 20 or basket assembly 50. Suitable sensors that may be used for sensor 140 include: thermocouples, fiber optics, resistive wires, thermocouple IR detectors, and the like. Suitable thermocouples for sensor 140 include: T type with copper constantene, J type, E type and K types as are well known those skilled in the art.

Temperature data from sensors 140 are fed back to control unit 136 and through an algorithm which is stored within a microprocessor memory of control unit 136. Instructions are sent to an electronically controlled micropump (not shown) to deliver fluid through the fluid lines at the appropriate flow rate and duration to provide control temperature at the electrode-tissue interface 130 (refer to FIG. 27).

The reservoir of control unit 136 may have the ability to control the temperature of the cooling solution 70 by either cooling the fluid or heating the fluid. Alternatively, a fluid reservoir 134 of sufficient size may be used in which the cooling solution 70 is introduced at a temperature at or near that of the normal body temperature. Using a thermally insulated reservoir 142, adequate control of the tissue temperature may be accomplished without need of refrigeration or heating of the cooling solution 70. The flow of cooling solution 70 is controlled by control unit 136 or another feedback control system (described herein) to provide temperature control at the electrode-tissue interface 130.

A second diagnostic phase may be included after the treatment is completed. This provides an indication of LES tightening treatment success, and whether or not a second phase of treatment, to all or only a portion of the esophagus, now or at some later time, should be conducted. The second diagnostic phase is accomplished through one or more of the following methods: (i) visualization, (ii) measuring the impendance, (iii) ultrasonography, (iv) temperature measurement, (v) measurement of LES tension and contractile force via manometry or (vi) mapping/measuring the frequency of gastric myoelectric activity including normal slow frequency waves, and gastric arrhythmias 17' including tachygastrias and bradygastrias. In the latter case, the clinician can use the quantitative analysis of gastric arrhythmias (e,g frequency, signal amplitude) 17' as both an indication of a TLSER and as means to titrate treatment and establish a clinical endpoint particularly in the case when doing gastric nerve ablation or creating areas of electrical block to pathways causing a TLSER. The detection and analysis of gastric arrhythmias 17' can be made using signal processing means described herein. The second diagnostic phase can also include stimulation to evoke a swallowing reflex using a stimulation device/means described herein to assure that the swallowing reflex and associated nerves are still functional.

Figure 30:
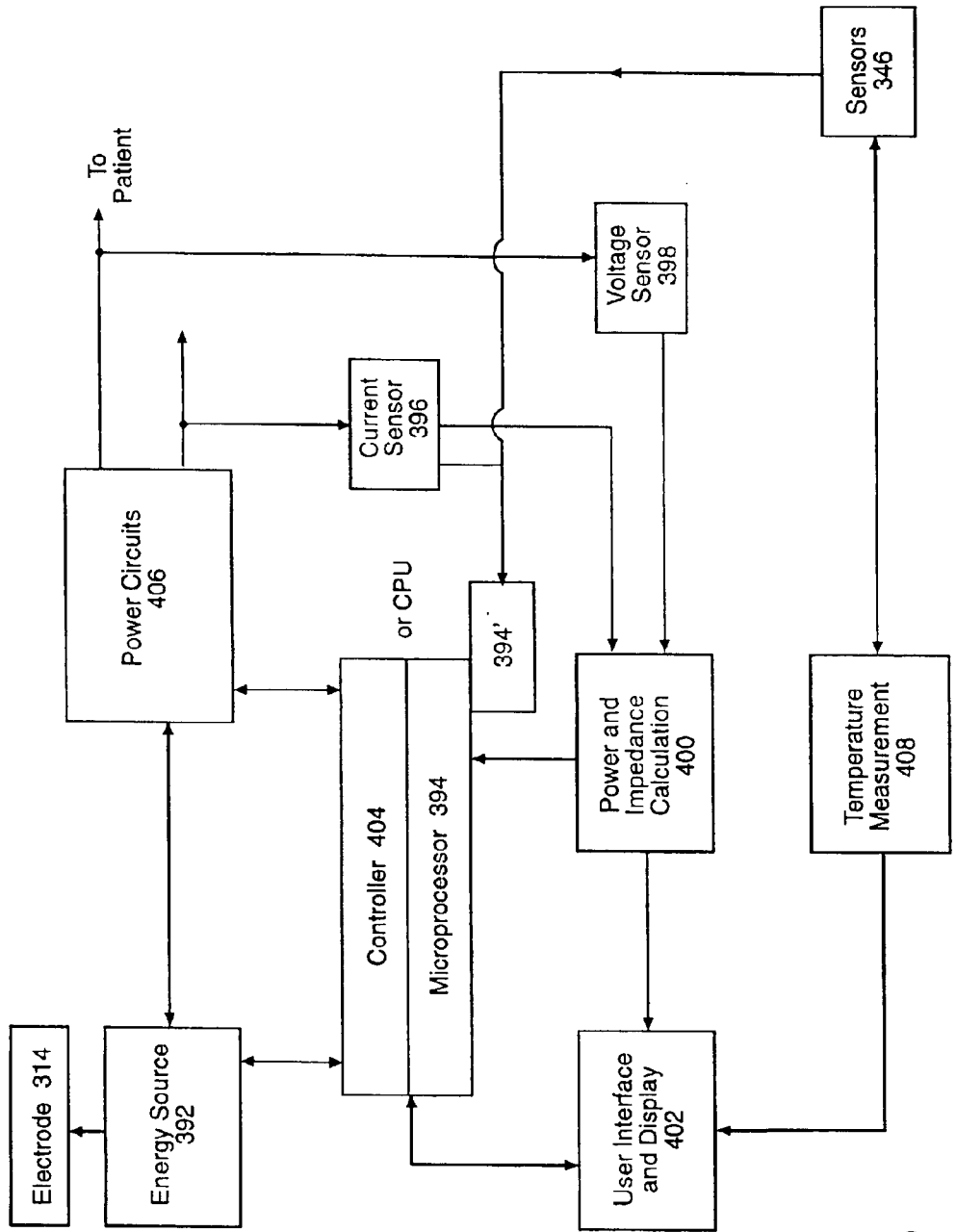
FIG. 30 depicts a block diagram of the feed back control system that can be used with the sphincter mapping and treatment apparatus.

In one embodiment, sphincter mapping and treatment apparatus 10 is coupled to an open or closed loop feedback system. Referring now to FIG. 30, an open or closed loop feedback system couples sensor 346 to energy/power source 392. In this embodiment, electrode 314 is one or more RF electrodes 314 and power source 392 is an RF generator.

The temperature of the tissue, or of RF electrode 314 is monitored, and the output power of energy source 392 adjusted accordingly. The physician can, if desired, override the closed or open loop system. A microprocessor 394 (also called controller 394 which can be the same as controller 24) can be included and incorporated in the closed or open loop system to switch power on and off, as well as modulate the power. The closed loop system utilizes microprocessor 394 to serve as a controller to monitor the temperature, adjust the RF power, analyze the result, refeed the result, and then modulate the power. More specifically, controller 394 governs the power levels, cycles, and duration that the radio frequency energy is distributed to the individual electrodes 314 to achieve and maintain power levels appropriate to achieve the desired treatment objectives and clinical endpoints. Controller 394 can also in tandem, govern the delivery of cooling fluid and, if desired, the removal of aspirated material. Microprocessor 394 can be integral to or otherwise coupled to power source 392. The controller 394 can include an input/output (I/O) device 394'. The I/O device 394' allows the physician to input control and processing variables, to enable the controller to generate appropriate command signals. The I/O device 394' also receives real time processing feedback information from one or more sensors associated with the operative element (as will be described later), for processing by the controller 394, e.g., to govern the application of energy and the delivery of processing fluid. The I/O device 394' may also include a user interface or graphical user interface (GUI), to graphically present processing information to the physician for viewing or analysis. As discussed herein, controller 394 can also be coupled to a fluid delivery apparatus and/or an aspirating apparatus.

With the use of sensor 346 and the feedback control system a tissue adjacent to RF electrode 314 can be maintained at a desired temperature for a selected period of time without causing a shut down of the power circuit to electrode 314 due to the development of excessive electrical impedance at electrode 314 or adjacent tissue as is discussed herein. Each RF electrode 314 is connected to resources which generate an independent output. The output maintains a selected energy at RF electrode 314 for a selected length of time.

Current delivered through RF electrode 314 is measured by current sensor 396. Voltage is measured by voltage sensor 398. Impedance and power are then calculated at power and impedance calculation device 400. These values can then be displayed at user interface and display 402. Signals representative of power and impedance values are received by a controller 404.

A control signal is generated by controller 404 that is proportional to the difference between an actual measured value, and a desired value. The control signal is used by power circuits 406 to adjust the power output in an appropriate amount in order to maintain the desired power delivered at respective RF electrodes 314.

In a similar manner, temperatures detected at sensor 346 provide feedback for maintaining a selected power. Temperature at sensor 346 is used as a safety means to interrupt the delivery of energy when maximum pre-set temperatures are exceeded. The actual temperatures are measured at temperature measurement device 408, and the temperatures are displayed at user interface and display 402. A control signal is generated by controller 404 that is proportional to the difference between an actual measured temperature and a desired temperature. The control signal is used by power circuits 406 to adjust the power output in an appropriate amount in order to maintain the desired temperature delivered at the sensor 346. A multiplexer can be included to measure current, voltage and temperature, at the sensor 346, and energy can be delivered to RF electrode 314 in monopolar or bipolar fashion.

Controller 404 can be a digital or analog controller, or a computer with software. When controller 404 is a computer it can include a CPU coupled through a system bus. This system can include a keyboard, a disk drive, or other non-volatile memory systems, a display, and other peripherals, as are known in the art. Also coupled to the bus is a program memory and a data memory.

User interface and display 402 includes operator controls and a display and may include a GUI interface as discussed herein. Controller 404 can be coupled to imaging systems including, but not limited to, ultrasound, CT scanners, X-ray, MRI, mammographic X-ray and the like. Further, direct visualization and tactile imaging can be utilized.

The output of current sensor 396 and voltage sensor 398 are used by controller 404 to maintain a selected power level at RF electrode 314. The amount of RF energy delivered controls the amount of power. A profile of the power delivered to electrode 314 can be incorporated in controller 404 and a preset amount of energy to be delivered may also be profiled.

Circuitry, software and feedback to controller 404 result in process control, the maintenance of the selected power setting which is independent of changes in voltage or current, and is used to change the following process variables: (i) the selected power setting, (ii) the duty cycle (e.g., on-off time), (iii) bipolar or monopolar energy delivery; and, (iv) fluid delivery, including flow rate and pressure. These process variables are controlled and varied, while maintaining the desired delivery of power independent of changes in voltage or current, based on temperatures monitored at sensor 346.

Figure 31:
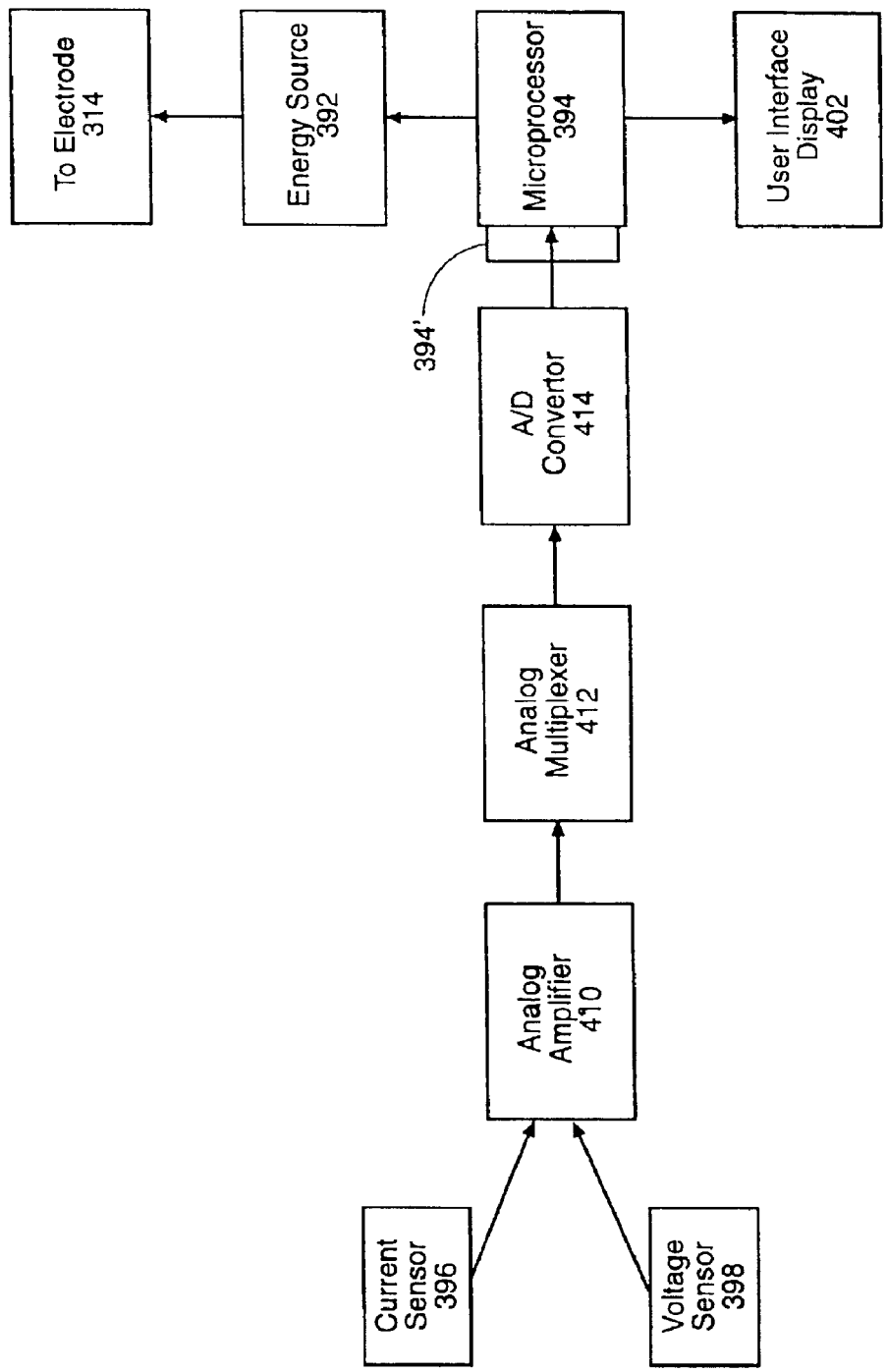
FIG. 31 depicts a block diagram of an analog amplifier, analog multiplexer and microprocessor used with the feedback control system of FIG. 30.

Referring now to FIG. 31, current sensor 396 and voltage sensor 398 are connected to the input of an analog amplifier 410. Analog amplifier 410 can be a conventional differential amplifier circuit for use with sensor 346. The output of analog amplifier 410 is sequentially connected by an analog multiplexer 412 to the input of A/D converter 414. The output of analog amplifier 410 is a voltage which represents the respective sensed temperatures. Digitized amplifier output voltages are supplied by A/D converter 414 to microprocessor 394. Microprocessor 394 may be a type 68HCII available from Motorola. However, it will be appreciated that any suitable microprocessor or general purpose digital or analog computer can be used to calculate impedance or temperature.

Microprocessor 394 sequentially receives and stores digital representations of impedance and temperature. Each digital value received by microprocessor 394 corresponds to different temperatures and impedances. Calculated power and impedance values can be indicated on user interface and display 402. Alternatively, or in addition to the numerical indication of power or impedance, calculated impedance and power values can be compared by microprocessor 394 to power and impedance limits. When the values exceed predetermined power or impedance values, a warning can be given on user interface and display 402, and additionally, the delivery of RF energy can be reduced, modified or interrupted. A control signal from microprocessor 394 can modify the power level supplied by energy source 392.

Figure 32:
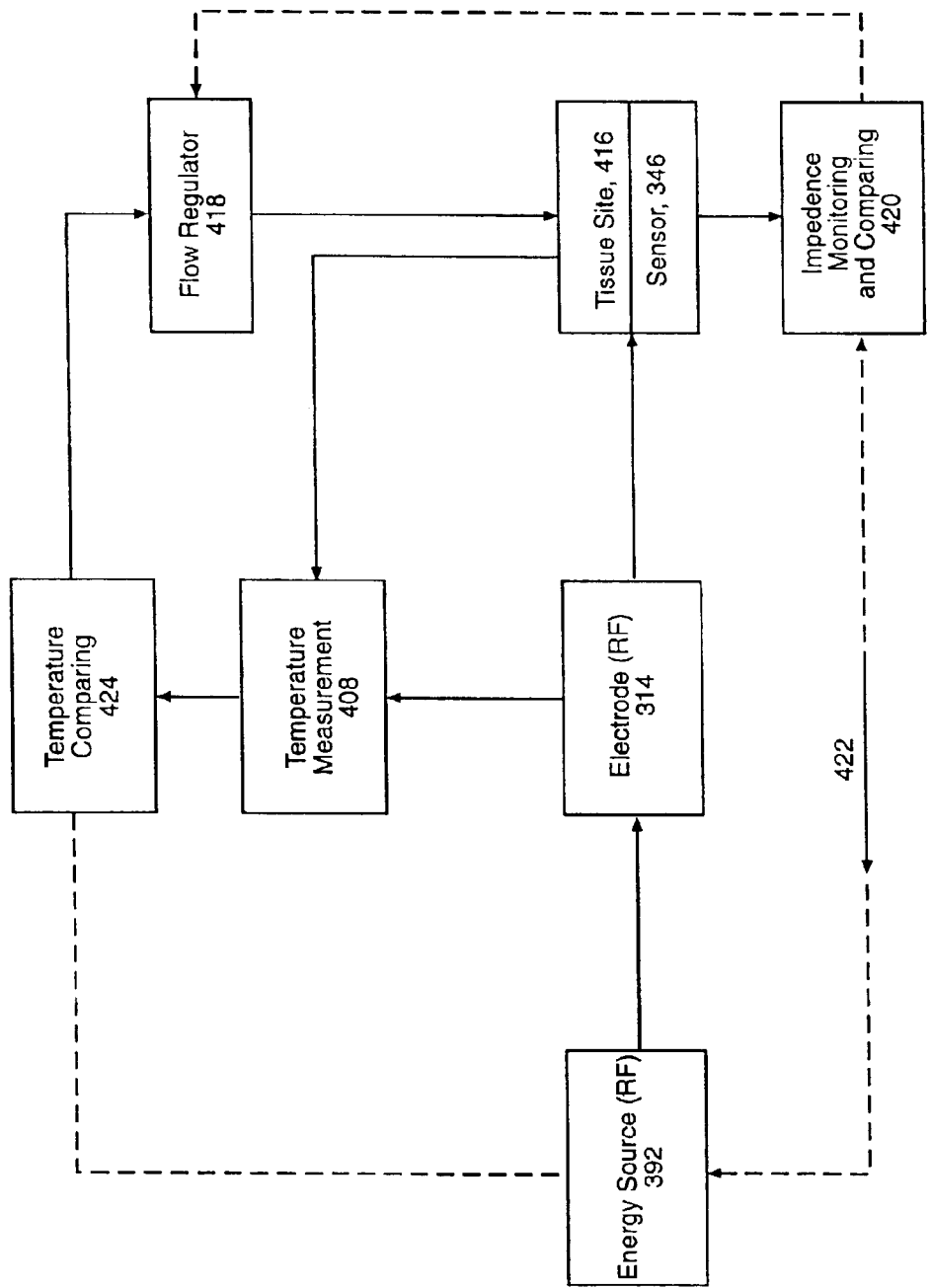
FIG. 32 depicts a block diagram of the operations performed in the feedback control system depicted in FIG. 30.

FIG. 32 illustrates a block diagram of a temperature and impedance feedback system that can be used to control the delivery of energy to tissue site 416 by energy source 392 and the delivery of cooling solution 70 to electrode 314 and/or tissue site 416 by flow regulator 418. Energy is delivered to RF electrode 314 by energy source 392, and applied to tissue site 416. A monitor 420 ascertains tissue impedance, based on the energy delivered to tissue, and compares the measured impedance value to a set value. If the measured impedance exceeds the set value, a disabling signal 422 is transmitted to energy source 392, ceasing further delivery of energy to RF electrode 314. If the measured impedance is within acceptable limits, energy continues to be applied to the tissue.

The control of cooling solution 70 to electrode 314 and/or tissue site 416 is done in the following manner. During the application of energy, temperature measurement device 408 measures the temperature of tissue site 416 and/or RF electrode 314. A comparator 424 receives a signal representative of the measured temperature and compares this value to a pre-set signal representative of the desired temperature. If the tissue temperature is too high, comparator 424 sends a signal to a flow regulator 418 (connected to an electronically controlled micropump, not shown) representing a need for an increased cooling solution flow rate. If the measured temperature has not exceeded the desired temperature, comparator 424 sends a signal to flow regulator 418 to maintain the cooling solution flow rate at its existing level.

This specification discloses various catheter-based systems and methods for treating dysfunction of sphincters and adjoining tissue regions in the body. The systems and methods are particularly well suited for treating these dysfunctions in the upper gastrointestinal tract, e.g., in the lower esophageal sphincter and adjacent structures of the stomach such as the cardia. The disclosed systems and methods are also applicable for use in treating other dysfunctions elsewhere in the body, which are not necessarily sphincter-related. For example, the various aspects of the invention have application in procedures requiring treatment of hemorrhoids, or incontinence, or restoring compliance to or otherwise tightening interior tissue or muscle regions. The systems and methods that embody features of the invention are also adaptable for use with systems and surgical techniques that are not necessarily catheter-based. Furthermore, this specification is not intended to be exhaustive or to limit the invention to the precise forms disclosed. Obviously, many modifications and variations will be apparent to practitioners skilled in this art.

Figure 33:
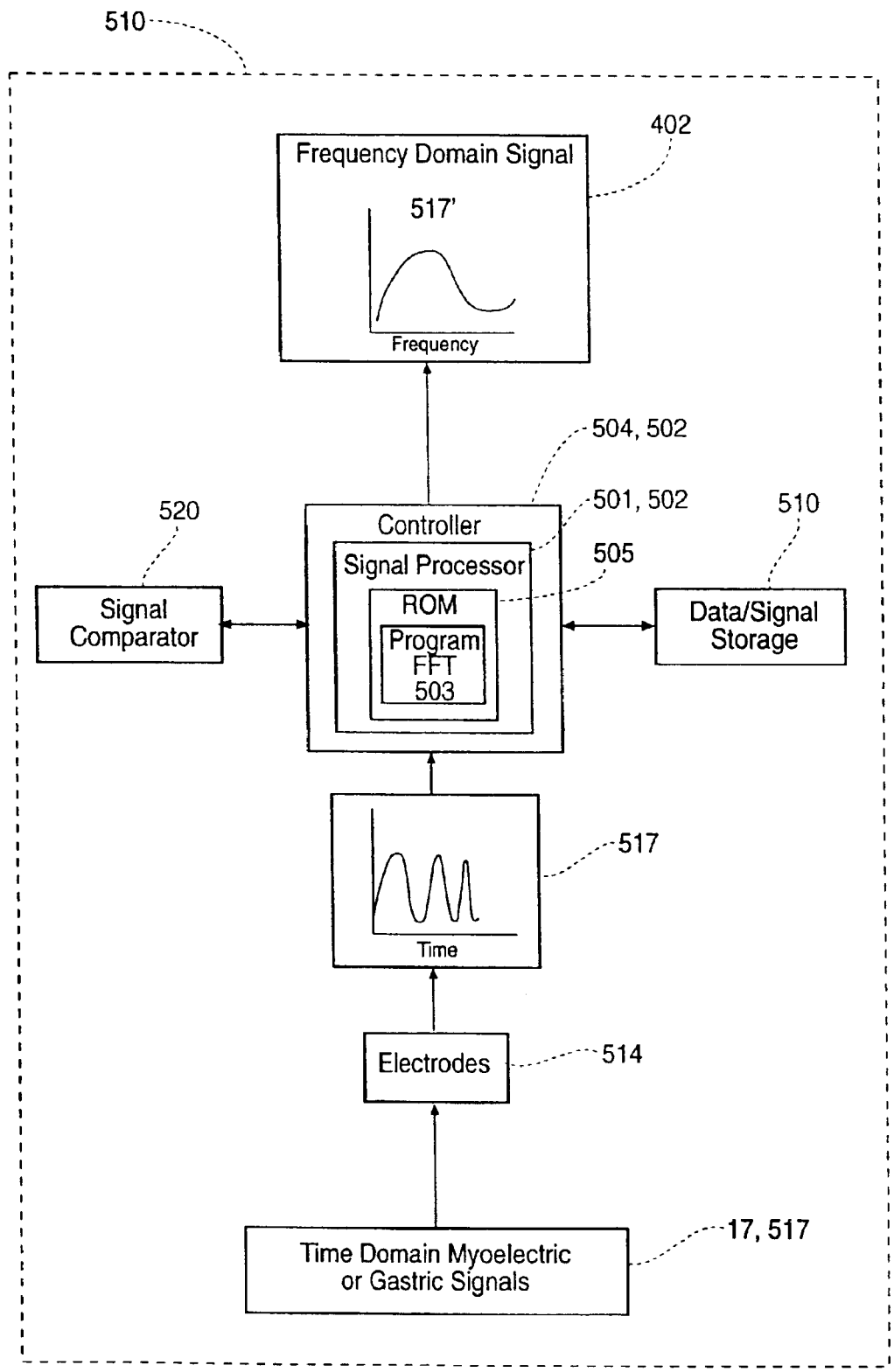
FIG. 33 depicts a block diagram of the signal processing system that can be used with the sphincter mapping and treatment apparatus.

In another embodiment shown in FIG. 33, apparatus 10 can be coupled to a signal processing system 500 which comprises a signal processor 501 that is integral to or otherwise couped to a controller 504. Signal processing means 501 in turn can be coupled to data/signal storage device 510 (also called memory resources 510) and signal comparitor means 520. Signal processor 501 is configured to take time domain bioelecectric signals/waveforms 517 detected by electrodes 514, (such as myoelectric or gastric signals 17 including those corresponding to or otherwise indicative of a TLESR) and convert them into frequency domain signal 517' in order to obtain information which can be displayed as a waveform indicative of the frequency of TLSERs or other myo/neuro gastric event, such as a peristaltic wave, stomach contraction, swallowing reflex. The output signal 517' of signal processor 501 can be coupled to and/or displayed on user interface 402. Signal processor 501 can also be used to calculate other wave related functions such as power spectral density and the like. Controller 504 serves to control the data exchange/handshake (both analog and digital) between signal processor 504, comparitors 520, and data storage device 510. Signal processor 501 or controller 504 can output signal 517' in either digital or analog form. In various embodiments controller 504 can be a mircroprocesser or application intergrated circuit (ASIC) which can include but is not limited to having intergral: processors, data bus, ROM, A/D converters, video processor, math processor, and input/output channels. In related embodiments, signal processing means 501 can be one or more microprocessors or integrated circuits 502 with electronically stored or embedded instructions sets or programs 503 for performing a mathematical transform (including a fourier or fast fourier transform (including a discrete FFT) or other wavelet transform function known in the art) to convert a time domain signal 517 (which can also be gastric signal 17) to a frequency domain signal 517', or vica versa. Processor 501 can also include but is not limited to having an integral data bus, ROM, A/D converter, video processor, math processor and input/output channels. In various embodiments, signal processor 501 or controller 504 can be a commercially available spectrum analyzer such as that made by the Hewlett Packard Corporation or a commercially available microprocessor such as an Intel® Pentium® or Pentium III® series, or a Motorolla® Power PC® series microprocessor. Processor 501 can be coupled to or have integral memory resources 505 which can be a Read Only Memory (ROM) chip containing stored or otherwise embedded programming for performing various signal processing functions including but not limited to fourier transforms, wavelet functions, filtering (e.g. high and low pass filtering) and signal averaging and the like.

Figure 34:
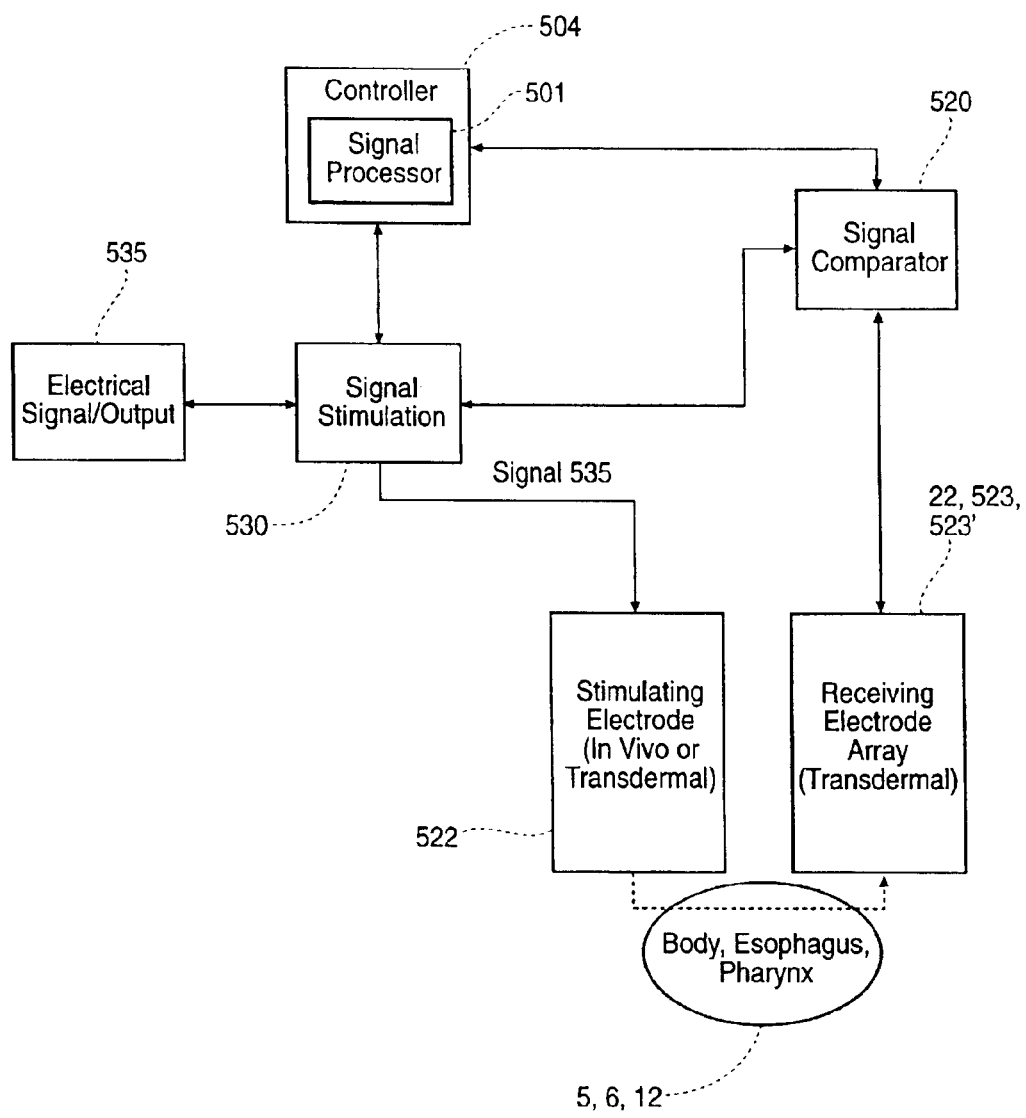
FIG. 34 depicts a block diagram of the transdermal signal stimulation system that can be used with the sphincter mapping and treatment apparatus.

In a related embodiment shown in FIG. 34, a signal stimulation means 530 can be coupled to signal processor 501. Signal stimulation means 530 generates a selectable electrical signal/output 535 sufficient to produce a TLESR, swallowing reflex, peristaltic wave or related myo/neuro esophageal or gastric event. Additionally signal stimulation means 530 can be configured to produce any number of evoked potentials or motor evoked potentials known in the art. In various embodiments, signal stimulation means 530 can be a commercially available medical electrical power supply such as DC or AC power supply available from the Hewlett Packard® Corporation, or a nerve stimulating device available from Danmeter A/S (Odense, Denmark) such as the Elfameter or one of the Neuro-Diagnostic product line available from the Medtronic® Corporation (Minneapolis, Minn.). A stimulating electrode 522 is electrically coupled to stimulation means 530 and can be the same as mapping electrode 22 or treatment electrode 22. In another embodiment, stimulating electrode 522 can be a transdermal electrode 523 placed on the abdomen epidermal layer overlying the LES or nearby. In this embodiment signal stimulation means 530 can is configured for producing a transdermal stimulating signal of sufficient amplitude and frequency for producing TLESR transdermally. Stimulation means 530 can be coupled to user interface 402 which can have user selected switching capability between in vivo and transdermal stimulation configurations. In various embodiments one electrode 522 can both be a mapping and receive electrode coupled to stimulation means 530 and signal comparitor means 520 (in this case signal stimulation means includes a time gating capability/algorithm for alternatively putting electrode 522 in a stimulating/transmitting mode and a mapping receiving mode. For embodiments with multiple electrodes 522, electrodes 522 can be multiplexed such that a portion are configured for stimulation and another portion are configured for mapping. For transdermal stimulation embodiments, electrode 522 on the apparatus 10 can be used as the receiving electrode or a separate transdermaly coupled electrode 523 (coupled to signal processing means 501) can be employed. In one embodiment transdermal receiving electrode 523 can be a plurality of electrodes 523' placed in larger area on the abdomen. The use of a plurality of electrodes improves signal detection, sensitivity and acquisition capability of signal processing means 501 for TLESR and other aberrant gastric signals. For transdermal embodiments, transdermal mapping and receiving electrodes 522 and 523 can be silver-silver chloride transdermal electrodes well known in the medical electronics art. In one transdermal embodiment, one or both of transdermal electrodes 523 and signal processing means 501 can be components from the Digitrapper™ EGG System available from the Medtronic® Corporation (Minneapolis, Minn.).

Figure 35:
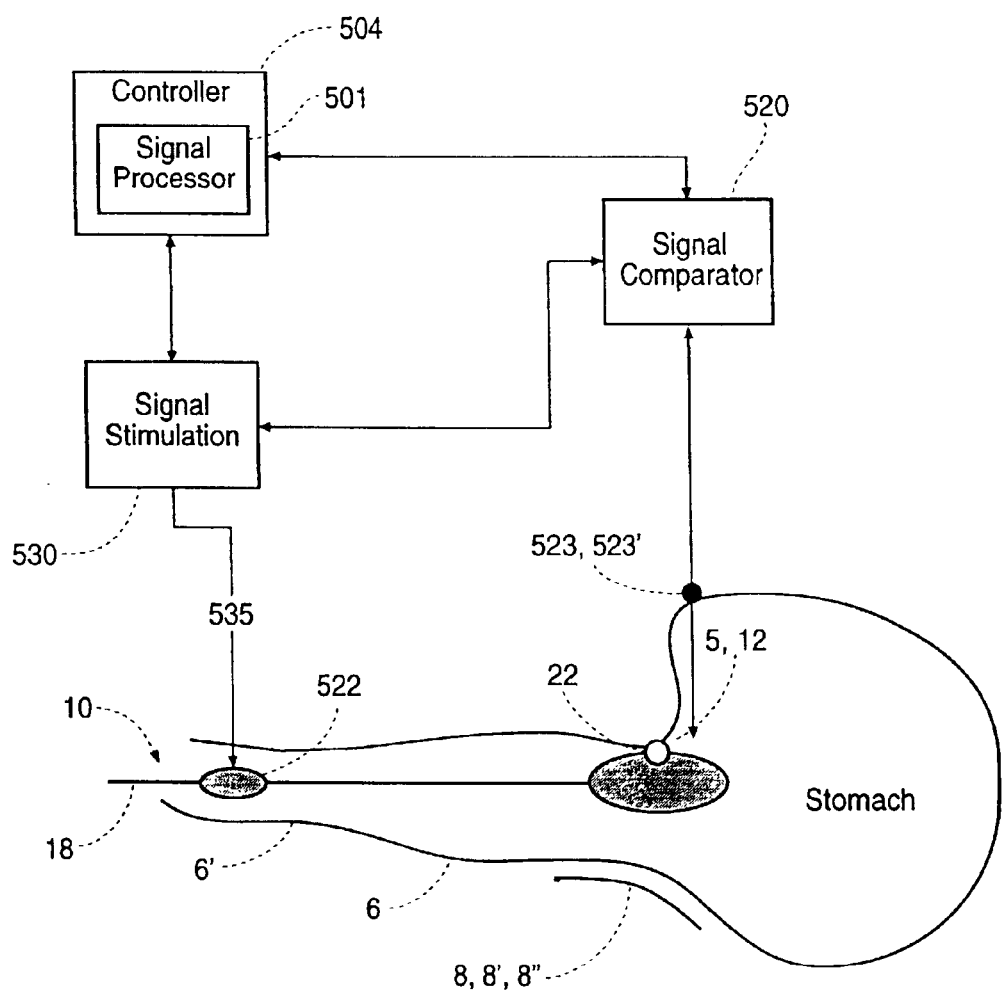
FIG. 35 depicts a block diagram of an embodiment of a signal stimulation system that can be used to evoke and monitor a swallowing reflex with one embodiment of the sphincter mapping and treatment apparatus.

In one embodiment depicted in FIG. 35, signal stimulation means 530 and signal processing means 501 are configured, to induce and/or monitor the presence of the swallowing reflex before, during or after the delivery of energy to the treatment site 12. This and related embodiments allow for the protection of a vagus 8" or other nerve 8, 8', 8" involved or associated in the swallowing reflex.

To facilitate such stimulation the stimulating electrode 522 can positioned on catheter 18 so as to be located in the more proximal/upper portions 6' of the esophagus 6 including the pharynx and oral cavity. In one embodiment, stimulating electrode 522 can be positioned proximal to mapping or treatment electrode 22. This allows for simultaneous stimulation of the upper esophagus 6' to produce a swallowing reflex or other myo-gastric event (e.g. perstaltic wave) while one or more of the following are performed: i) observation (by endoscopic, visual or other means) in the esophagus or LES for the swallowing reflex and/or opening of the LES, ii) mapping/sensing of the swallowing reflex, TLSER or other myo-gastric event and iii) delivery of energy to treatment site 12 in the LES 6 or other upper GI site. In other embodiments, stimulating electrode 522 can be positioned anywhere along the length of catheter 18 including basket assembly 20. In these and related embodiments, the signal stimulating electrode 522 can be used to evoke a swallowing reflex before or during the delivery of treatment to assure the integrity of swallowing reflex and related nerves and then subsequently afterward treatment to assure the same.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. An apparatus, comprising a treatment device including at least one of a mapping electrode or a treatment electrode, the treatment device being sized and configured for introduction into at least a portion of a tissue region comprising at least one of a sphincter, a lower esophageal sphincter, a stomach, a cardia or a fundus;

means for stimulating the tissue region to produce a transient relaxation of at least a portion of one of the sphincter, the lower esophageal sphincter, the stomach, the cardia or the fundus;

means coupled to the treatment device for identifying a portion of one of the sphincter, the lower esophageal sphincter, the stomach, the cardia or the fundus causing the transient relaxation; and means coupled to the treatment device for delivering energy from the the mapping electrod or the treatment electrode to treat the portion of one the sphincter, the lower esophageal sphincter, the stomach, the cardia or the fundus causing the transient relaxation.

2. The apparatus of claim 1, wherein the means for stimulating includes one of an electrical stimulation, a mechanical stimulation, a stretch stimulation or a chemical stimulation.

3. The apparatus of claim 1, further comprising means for performing a post treatment stimulation on one of the sphincter, the lower esophageal sphincter, the stomach, the cardia or the fundus; and means for assessing an effectiveness of treatment in preventing the transient relaxation.

4. The apparatus of claim 1, wherein the means for stimulating includes one of an external stimulation device or an internal stimulation device, wherein the external stimulation device is positionable on the skin near the stomach or wherein the internal stimulation device is positionable in the portion of one the sphincter, the lower esophageal sphincter, the stomach, the cardia or the fundus.

5. The apparatus of claim 4 wherein the means stimulating includes one of an internal stimulation or a transdermal stimulation.

6. An apparatus comprising a treatment device having at least one of a mapping electrode or a treatment electrode, the treatment device being sized and configured for introduction into at least a portion of a tissue region comprising at least one of a sphincter, a lower esophageal sphincter, a stomach, a cardia or a fundus;

means coupled to the treatment device for detecting an electrical activity causing a transient relaxation of at least a portion of the sphincter, the lower esophageal sphincter, the stomach, the cardia or the fundus;

means coupled to the treatment device for delivering energy to treat the electrical activity; and means coupled to the treatment device for mapping the tissue region after the treatment to assess the effectiveness of the treatment.

7. An apparatus for comprising a treatment device having at least one of a mapping electrode or a treatment electrode, the treatment device being sized and configured for introduction into at least a portion of one of sphincter, a lower esophageal sphincter, a stomach, a cardia or a fundus;

means for detecting a bioelectric activity causing a transient relaxation of at least a portion of the sphincter, the stomach, the cardia or the fundus; and means for delivering energy from the treatment delivery device to treat the bioelectric activity;

the treatment device comprising a basket assembly including a first and a second arm, the basket assembly being coupled to an elongated member and having a deployed and a non-deployed configuration;

an inflatable member coupled to the elongated member and positioned in an interior of the basket assembly, the inflatable member being coupled to an inflation lumen, the inflatable member having a deployed stare and a non-deployed state, wherein in the deployed state the inflatable member expands the basket assembly to the basket assembly deployed configuration;

a first energy delivery device positionable in the first arm and advanceable from the first arm to a selected treatment site; and a second energy delivery device positionable in the second arm and advanceable from the second arm to a selected treatment site;

at least one of the first and second energy delivery device adapted being to adapted to deliver RF energy to a treatment site in one of the sphincter, the lower esophageal sphincter, the stomach, the cardia or the fundus to at least partially ablate one of a nerve pathway, an afferent pathway, a electrical pathway, a mechanoreceptor pathway or a chemoreceptor pathway.

* * * * *

UNITED STATES PATENT AND TRADEMARK OFFICE
CERTIFICATE OF CORRECTION

PATENT NO. : 6,974,456 B2 Page 1 of 1
APPLICATION NO. : 10/156505
DATED : December 13, 2005
INVENTOR(S) : Stuart D. Edwards, John W. Gaiser and David S. Utley It is certified that error appears in the above-identified patent and that said Letters Patent is hereby corrected as shown below:

On the title page under item [56] "References Cited" insert -- 5,423,811 06/1995 Imran et al. --

Column 24, line 29, after "means" insert -- for --

Column 24, line 47, after "apparatus" delete "for"

Column 24, line 51, after "one of" insert -- a --

Column 24, line 66, after "having a deployed" delete "stare" and substitute -- state --

Column 26, line 1, after "delivery" delete "device" and substitute -- devices --

Column 26, line 2, delete "adapted being to adapted" and substitute -- being adapted to--

Signed and Sealed this

Twentieth Day of March, 2007

JON W. DUDAS
*Director of the United States Patent and Trademark Office*